(12) United States Patent
Guarraia et al.

(10) Patent No.: US 10,258,790 B2
(45) Date of Patent: Apr. 16, 2019

(54) SYSTEMS FOR PROVIDING NON-INVASIVE NEUROREHABILITATION OF A PATIENT

(71) Applicant: Neurohabilitation Corporation, Newtown, PA (US)

(72) Inventors: Mark Guarraia, Cranston, RI (US); Adam Muratori, Greenville, RI (US); Justin Fisk, Providence, RI (US); Aidan Petrie, Jamestown, RI (US); Jeffrey M. Wallace, Saunderstown, RI (US); Daniel P. Smith, Portsmouth, RI (US)

(73) Assignee: Helius Medical, Inc., Newtown, PA (US)

( * ) Notice: Subject to any disclaimer, the term of this patent is extended or adjusted under 35 U.S.C. 154(b) by 0 days.

(21) Appl. No.: 15/484,077

(22) Filed: Apr. 10, 2017

(65) Prior Publication Data

US 2017/0216578 A1    Aug. 3, 2017

Related U.S. Application Data

(63) Continuation of application No. 14/727,100, filed on Jun. 1, 2015, now Pat. No. 9,616,222, which is a
(Continued)

(51) Int. Cl.
*A61N 1/36* (2006.01)
*A61N 1/05* (2006.01)
*A61N 1/04* (2006.01)

(52) U.S. Cl.
CPC ......... *A61N 1/0548* (2013.01); *A61N 1/0456* (2013.01); *A61N 1/0476* (2013.01);
(Continued)

(58) Field of Classification Search
None
See application file for complete search history.

(56) References Cited

U.S. PATENT DOCUMENTS

| 2,055,540 A | 9/1936 | Karnofsky |
| 3,851,651 A | 12/1974 | Icenbice |

(Continued)

FOREIGN PATENT DOCUMENTS

| EP | 2671612 A1 | 12/2013 |
| KR | 20110038314 A | 4/2011 |

(Continued)

OTHER PUBLICATIONS

Danilov, Y.P. et al., "Emerging Noninvasive Neurostimulation Technologies: CN-NINM and Sympatocorection," Journal of Behavioral and Brain Science, 2014, 9 pages (pp. 105-113).

(Continued)

*Primary Examiner* — Kennedy Schaetzle
(74) *Attorney, Agent, or Firm* — Proskauer Rose LLP

(57) ABSTRACT

A system for providing non-invasive neuromodulation to a patient includes a mouthpiece and a controller. The mouthpiece includes an elongated housing, a printed circuit board, control circuitry mounted within the elongated housing, and a cable for connecting to a controller. The controller includes an elongated u-shaped element, an electronic receptacle, and a microcontroller. A method for providing non-invasive neurorehabilitation of a patient including connecting a mouthpiece to a controller, transmitting a numeric sequence to the mouthpiece, generating a first hash code, transmitting the first hash code to the controller, generating a second hash code, comparing the second hash code with the first hash code, enabling electrical communication between the mouthpiece and the controller only if the first hash code matches the second hash code, contacting the mouthpiece
(Continued)

with the patient's intraoral cavity, and delivering neurostimulation to the patient's intraoral cavity.

10 Claims, 17 Drawing Sheets

Related U.S. Application Data continuation-in-part of application No. 14/558,768, filed on Dec. 3, 2014, now Pat. No. 9,072,889.

(52) U.S. Cl.
CPC ....... *A61N 1/0529* (2013.01); *A61N 1/36014* (2013.01); *A61N 1/36025* (2013.01); *A61N 1/0484* (2013.01)

(56) References Cited

U.S. PATENT DOCUMENTS

| | | | |
|---|---|---|---|
| 4,865,048 | A | 9/1989 | Eckerson |
| 4,924,880 | A | 5/1990 | O'Neill et al. |
| 4,995,404 | A | 2/1991 | Nemir |
| 5,259,762 | A | 11/1993 | Farrell |
| 5,265,624 | A | 11/1993 | Bowman |
| 5,269,303 | A | 12/1993 | Wernicke et al. |
| 5,299,569 | A | 4/1994 | Wernicke et al. |
| 5,540,734 | A | 7/1996 | Zabara |
| 5,553,626 | A | 9/1996 | Burger et al. |
| 5,792,067 | A | 8/1998 | Karell |
| 5,794,621 | A | 8/1998 | Hogan et al. |
| 5,878,154 | A | 3/1999 | Schimmelpfennig |
| D409,307 | S | 5/1999 | Phleps et al. |
| 6,066,163 | A | 5/2000 | John |
| 6,089,864 | A | 7/2000 | Buckner et al. |
| 6,161,044 | A | 12/2000 | Silverstone |
| D437,058 | S | 1/2001 | Gozani |
| 6,169,781 | B1 | 1/2001 | Doebert et al. |
| 6,267,733 | B1 | 7/2001 | Peterson et al. |
| D449,376 | S | 10/2001 | McDonald et al. |
| D449,883 | S | 10/2001 | McDonald et al. |
| D451,598 | S | 12/2001 | McDonald et al. |
| 6,326,901 | B1 | 12/2001 | Gonzales |
| 6,339,725 | B1 | 1/2002 | Naritoku et al. |
| 6,366,813 | B1 | 4/2002 | DiLorenzo |
| 6,366,814 | B1 | 4/2002 | Boveja et al. |
| 6,405,079 | B1 | 6/2002 | Ansarinia |
| 6,430,450 | B1 | 8/2002 | Bach-y-Rita et al. |
| D462,357 | S | 9/2002 | Jenkins |
| 6,463,328 | B1 | 10/2002 | John |
| 6,526,318 | B1 | 2/2003 | Ansarinia |
| 6,546,291 | B2 | 4/2003 | Merfeld et al. |
| 6,556,868 | B2 | 4/2003 | Naritoku et al. |
| 6,954,668 | B1 | 10/2005 | Cuozzo |
| D515,697 | S | 2/2006 | Nakamura et al. |
| D531,314 | S | 10/2006 | Atkinson et al. |
| D542,408 | S | 5/2007 | Oldenburg et al. |
| 7,228,178 | B2 | 6/2007 | Carroll et al. |
| 7,236,830 | B2 | 6/2007 | Gliner |
| D555,252 | S | 11/2007 | Kitayama et al. |
| D557,685 | S | 12/2007 | Lee |
| 7,333,020 | B2 | 2/2008 | Cohen et al. |
| D565,184 | S | 3/2008 | Royzen |
| D575,268 | S | 8/2008 | Christopher |
| D578,222 | S | 10/2008 | Sakurai |
| D579,552 | S | 10/2008 | Oldenburg et al. |
| 7,483,747 | B2 | 1/2009 | Gliner et al. |
| D593,067 | S | 5/2009 | Millora et al. |
| 7,563,929 | B2 | 7/2009 | Hobbs et al. |
| 7,565,200 | B2 | 7/2009 | Wyler et al. |
| 7,640,062 | B2 | 12/2009 | Shalev |
| 7,672,730 | B2 | 3/2010 | Firlik et al. |
| 7,725,192 | B2 | 5/2010 | Eskandar et al. |
| D617,308 | S | 6/2010 | Nousiainen et al. |
| 7,747,325 | B2 | 6/2010 | DiLorenzo |
| D624,189 | S | 9/2010 | Rutt et al. |
| D663,714 | S | 7/2012 | Kang et al. |
| D669,881 | S | 10/2012 | Clements et al. |
| 8,290,582 | B2 | 10/2012 | Lin et al. |
| D687,018 | S | 7/2013 | Afshar |
| D706,745 | S | 6/2014 | Nakagawa |
| D707,199 | S | 6/2014 | Cepress et al. |
| D709,673 | S | 7/2014 | Aimone et al. |
| D710,718 | S | 8/2014 | Ichihashi et al. |
| 8,805,548 | B2 | 8/2014 | Mignolet et al. |
| D713,531 | S | 9/2014 | Way et al. |
| 8,849,407 | B1 | 9/2014 | Danilov et al. |
| D716,759 | S | 11/2014 | Ha et al. |
| D721,673 | S | 1/2015 | Park et al. |
| D723,510 | S | 3/2015 | Ishikura |
| D724,197 | S | 3/2015 | Hughes |
| D725,262 | S | 3/2015 | Chowdhury |
| D728,109 | S | 4/2015 | Ko |
| D730,867 | S | 6/2015 | Park |
| D731,999 | S | 6/2015 | Cepress et al. |
| 9,072,889 | B1 | 7/2015 | Guarraia et al. |
| D739,122 | S | 9/2015 | Aimone et al. |
| 9,124,979 | B2 | 9/2015 | O'Grady et al. |
| D744,658 | S | 12/2015 | Hilkey-Boyatt |
| 9,789,306 | B2 * | 10/2017 | Sabourin ............ A61N 1/36025 |
| 2003/0220677 | A1 | 11/2003 | Doan et al. |
| 2004/0073270 | A1 | 4/2004 | Firlik et al. |
| 2004/0073271 | A1 | 4/2004 | Harry et al. |
| 2005/0089829 | A1 | 4/2005 | Wasowicz |
| 2005/0197529 | A1 | 9/2005 | Hoshihara et al. |
| 2005/0203582 | A1 * | 9/2005 | Healy ................ A61N 1/37211 607/31 |
| 2005/0240253 | A1 | 10/2005 | Tyler et al. |
| 2006/0161218 | A1 | 7/2006 | Danilov |
| 2006/0241718 | A1 | 10/2006 | Tyler et al. |
| 2007/0248238 | A1 | 10/2007 | Abreu |
| 2007/0250119 | A1 | 10/2007 | Tyler et al. |
| 2007/0293917 | A1 | 12/2007 | Thompson et al. |
| 2007/0293918 | A1 | 12/2007 | Thompson et al. |
| 2008/0009772 | A1 | 1/2008 | Tyler et al. |
| 2008/0027510 | A1 | 1/2008 | McClure et al. |
| 2008/0082131 | A1 | 4/2008 | Llanos |
| 2008/0208287 | A1 | 8/2008 | Palermo et al. |
| 2008/0222670 | A1 | 9/2008 | Lee et al. |
| 2008/0228239 | A1 | 9/2008 | Tyler et al. |
| 2008/0233541 | A1 | 9/2008 | De Vreese et al. |
| 2008/0234604 | A1 * | 9/2008 | Burgmans ............ A61B 5/4017 600/582 |
| 2008/0281550 | A1 | 11/2008 | Hogle et al. |
| 2009/0048647 | A1 | 2/2009 | Tingey |
| 2009/0082831 | A1 | 3/2009 | Paul et al. |
| 2009/0082839 | A1 | 3/2009 | Lindquist et al. |
| 2009/0312808 | A1 | 12/2009 | Tyler et al. |
| 2009/0312817 | A1 | 12/2009 | Hogle et al. |
| 2009/0326604 | A1 | 12/2009 | Tyler et al. |
| 2011/0093036 | A1 | 4/2011 | Mashiach |
| 2011/0125184 | A1 | 5/2011 | Allen |
| 2011/0201944 | A1 | 8/2011 | Higgins et al. |
| 2012/0010672 | A1 | 1/2012 | Crespi |
| 2012/0123225 | A1 | 5/2012 | Al-Tawil |
| 2012/0165862 | A1 | 6/2012 | Allen |
| 2013/0096641 | A1 | 4/2013 | Strother et al. |
| 2013/0256345 | A1 | 10/2013 | Larkin |
| 2013/0273490 | A1 | 10/2013 | Way et al. |
| 2014/0039579 | A1 | 2/2014 | Mashiach et al. |
| 2014/0135868 | A1 | 5/2014 | Bashyam |
| 2014/0172041 | A1 | 6/2014 | Draghici et al. |
| 2014/0194946 | A1 | 7/2014 | Thomas et al. |
| 2014/0379049 | A1 | 12/2014 | Mashiach et al. |
| 2015/0057719 | A1 | 2/2015 | Tang |
| 2015/0264474 | A1 | 9/2015 | Seo et al. |

FOREIGN PATENT DOCUMENTS

| | | |
|---|---|---|
| RU | 2215558 C2 | 11/2003 |
| RU | 2248227 C1 | 3/2005 |
| SU | 1068128 A | 1/1984 |

(56) References Cited

FOREIGN PATENT DOCUMENTS

| WO | 02066111 A1 | 8/2002 |
| WO | 2013172935 A2 | 11/2013 |
| WO | 2014150090 A1 | 9/2014 |

OTHER PUBLICATIONS

Helius Medical Technologies, Inc., "Interchange PoNS Unit," Listing Statement, Form 2A, Jun. 20, 2014, 3 pages.

Helius Medical Technologies, Inc., "The PoNS Device," www.heliusmedical.com/divisions/neurohabilitation/pons-device, last visited Dec. 2, 2015, 4 pages.

Sidyakina I.V., "Swallowing rehabilitation of patients with serious diseases and brain injuries," Restorative medicine bulletin, 2011, No. 4, pp. 14-17.

Tyler, M.E. et al., "Non-invasive neuromodulation to improve gait in chronic multiple sclerosis: a randomized double blind controlled pilot trial," Journal of Neuroengineering and Rehabilitation, 2014, 10 pages.

US Army "Mouth Device in Clinical Trials as Possible Treatment for TBI," https://www.army.mil/article/96521 (last visited Dec. 2, 2015), Feb. 14, 2013, 2 pages.

Hamilton, "Impact of Acoustic and Tactile Multi-Modal Stimulation on Objective and Subjective Measures of Permanent Intractable Tinnitus: A Prospective Research Study," Hamilton Institute, National University of Ireland Maynooth, Jun. 2014.

"Systems and Methods for Providing Non-Invasive Neurorehabilitation of a Patient" Specification, Drawings, and Prosecution History of U.S. Appl. No. 14/558,784, filed Dec. 3, 2014, by Sabourin et al.

\* cited by examiner

SYSTEMS FOR PROVIDING NON-INVASIVE NEUROREHABILITATION OF A PATIENT

CROSS-REFERENCE TO RELATED APPLICATIONS

This application is a continuation of U.S. patent application Ser. No. 14/727,100, filed Jun. 1, 2015, now U.S. Pat. No. 9,616,222, which is a continuation-in-part of U.S. patent application Ser. No. 14/558,768, filed Dec. 3, 2014, now U.S. Pat. No. 9,072,889, both of which are incorporated by reference herein in their entireties.

FIELD OF THE INVENTION

In general, the invention relates to devices and methods for non-invasive neurostimulation of a subject's brain. More specifically, the invention relates to devices and methods for non-invasive neurostimulation of a subject's brain to effect treatment of various maladies.

BACKGROUND OF THE INVENTION

Traumatic brain injury (TBI) is a leading cause of disability around the world. Each year in the United States, about two million people suffer a TBI, with many suffering long term symptoms. Long term symptoms can include impaired attention, impaired judgment, reduced processing speed, and defects in abstract reasoning, planning, problem-solving and multitasking.

A stroke is a loss of brain function due to a disturbance in the blood supply to the brain. Every year, about 800,000 people in the United States will have a stroke. Stroke is a leading cause of long-term disability in the United States, with nearly half of older stroke survivors experiencing moderate to severe disability. Long term effects can include seizures, incontinence, vision disturbance or loss of vision, dysphagia, pain, fatigue, loss of cognitive function, aphasia, loss of short-term and/or long-term memory, and depression.

Multiple sclerosis (MS) is a disease that causes damage to the nerve cells in the brain and spinal cord. Globally, there are about 2.5 million people who suffer from MS. Symptoms can vary greatly depending on the specific location of the damaged portion of the brain or spinal cord. Symptoms include hypoesthesia, difficulties with coordination and balance, dysarthria, dysphagia, nystagmus, bladder and bowel difficulties, cognitive impairment and major depression to name a few.

Alzheimer's disease (AD) is a neurodegenerative disorder affecting over 25 million people worldwide. Symptoms of AD include confusion, irritability, aggression, mood swings, trouble with language, and both short and long term memory loss. In developed countries, AD is one of the most costly diseases to society.

Parkinson's disease (PD) is a degenerative disorder of the central nervous system, affecting more than 7 million people globally. Symptoms of PD include tremor, bradykinesia, rigidity, postural instability, cognitive disturbances, and behavior and mood alterations.

One approach to treating the long term symptoms associated with TBI, stroke, MS, AD, and PD is neurorehabilitation. Neurorehabilitation involves processes designed to help patients recover from nervous system injuries. Traditionally, neurorehabilitation involves physical therapy (e.g., balance retraining), occupational therapy (e.g., safety training, cognitive retraining for memory), psychological therapy, speech and language therapy, and therapies focused on daily function and community re-integration.

Another approach to treating the long term symptoms associated with TBI, stroke, MS, AD, and PD is neurostimulation. Neurostimulation is a therapeutic activation of part of the nervous system. For example, activation of the nervous system can be achieved through electrical stimulation, magnetic stimulation, or mechanical stimulation. Typical approaches focused mainly on invasive techniques, such as deep brain stimulation (DBS), spinal cord stimulation (SCS), cochlear implants, visual prosthesis, and cardiac electrostimulation devices. Only recently have non-invasive approaches to neurostimulation become more mainstream.

Despite many advances in the areas of neurorehabilitation and neurostimulation, there exists an urgent need for treatments that employ a combined approach, including both neurorehabilitation and neurostimulation to improve the recovery of patients having TBI, stroke, multiple sclerosis, Alzheimer's, Parkinson's or any other neurological impairment.

SUMMARY OF THE INVENTION

The invention, in various embodiments, features methods and devices for combining non-invasive neuromodulation with traditional neurorehabilitation therapies. Clinical studies have shown that methods combining neurostimulation with neurorehabilitation are effective in treating the long term neurological impairments due to a range of maladies such as TBI, stroke, MS, AD, and PD.

In one aspect, the invention features a system for providing non-invasive neuromodulation to a patient. The system includes a mouthpiece and a controller. The mouthpiece includes an elongated housing having an anterior region and a posterior region, the elongated housing having a non-planar exterior top surface. The mouthpiece also includes a printed circuit board mounted to a bottom portion of the elongated housing, the printed circuit board having a plurality of electrodes for delivering subcutaneous local electrical stimulation to the patient's tongue. The mouthpiece also includes control circuitry mounted within a top portion of the elongated housing for controlling electrical signals delivered to the electrodes. The mouthpiece also includes a cable with a first end attached to the anterior portion of the elongated housing and having a connector at a second end for connecting to a controller, the cable delivering electrical current to the electrodes via the control circuitry. The controller includes an elongated u-shaped element configured to rest upon a patient's shoulders. The controller also includes an electronic receptacle located at a terminus of the u-shaped element connecting to the cable. The controller also includes a microcontroller located within the three-dimensional u-shaped element, the microcontroller configured to send electrical control signals to the mouthpiece, the electrical control signals determining an amplitude and duration of electrical signals delivered to the patient's tongue.

In some embodiments, the system also includes an accelerometer for measuring an activity level of the patient. In some embodiments, the system also includes a data logger for logging information related to the activity level of the patient. In some embodiments, the system also includes tongue sense circuitry for determining if a patient's tongue is in contact with the plurality of electrodes located on the bottom portion of the mouthpiece. In some embodiments, the system also includes a real time clock for determining a total time of usage of the mouthpiece. In some embodiments, the system also includes a battery for providing a current to the mouthpiece. In some embodiments, the system also includes an optical indicator that indicates a power level of the battery. In some embodiments, the system also includes an audio indicator that can warn the patient when the remaining battery charge is inadequate to complete a therapy session. In some embodiments, the exterior top surface of the elongated housing is planar. In some embodiments, the printed circuit board is mounted to a middle or top portion of the elongated housing. In some embodiments, the control circuitry is mounted within a middle or top portion of the elongated housing. In some embodiments, the cable is permanently attached to the controller and is removably attached to the mouthpiece.

In another aspect, the invention features a system for providing non-invasive neuromodulation to a patient. The system includes a mouthpiece and a controller. The mouthpiece includes an elongated housing having an anterior region and a posterior region, the elongated housing having a non-planar exterior top surface. The mouthpiece also includes a printed circuit board mounted to the elongated housing, the printed circuit board having a plurality of electrodes for delivering subcutaneous local electrical stimulation to the patient's tongue. The mouthpiece also includes control circuitry mounted within the elongated housing for controlling electrical signals delivered to the electrodes. The mouthpiece also includes a first communication module delivering electrical current to the electrodes via the control circuitry. The controller includes an elongated u-shaped housing configured to rest upon a patient's shoulders. The controller also includes a second communication module within the housing coupled to and in communication with the first communication module. The controller also includes a microcontroller located within the housing and configured to exchange electrical signals with the mouthpiece, the electrical signals determining an amplitude and duration of electrostimulation energy pulses delivered to the patient's tongue.

In some embodiments, the system also includes an accelerometer for measuring an activity level of the patient. In some embodiments, the system also includes a data logger for logging information related to the activity level of the patient. In some embodiments, the system also includes tongue sense circuitry for determining if a patient's tongue is in contact with the plurality of electrodes located on the bottom portion of the mouthpiece. In some embodiments, the system also includes a real time clock for determining a total time of usage of the mouthpiece. In some embodiments, the system also includes a battery for providing a current to the mouthpiece. In some embodiments, the system also includes an optical indicator that indicates a power level of the battery. In some embodiments, the system also includes an audio indicator that can warn the patient when the remaining battery charge is inadequate to complete a therapy session.

In yet another aspect, the invention features a system for providing non-invasive neuromodulation to a patient. The system includes a mouthpiece. The mouthpiece includes an elongated housing having an anterior region and a posterior region, the elongated housing having a non-planar exterior top surface. The mouthpiece also includes a printed circuit board mounted to a bottom portion of the elongated housing, the printed circuit board having a plurality of electrodes for delivering subcutaneous local electrical stimulation to the patient's tongue. The mouthpiece also includes control circuitry mounted within a top portion of the elongated housing for controlling electrical signals delivered to the electrodes. The system also includes a mobile device configured to send electrical control signals to the mouthpiece, the electrical control signals determining an amplitude and duration of electrical signals delivered to the patient's tongue.

In some embodiments, the system also includes an accelerometer for measuring an activity level of the patient. In some embodiments, the system also includes a data logger for logging information related to the activity level of the patient. In some embodiments, the system also includes tongue sense circuitry for determining if a patient's tongue is in contact with the plurality of electrodes located on the bottom portion of the mouthpiece. In some embodiments, the system also includes a real time clock for determining a total time of usage of the mouthpiece. In some embodiments, the system also includes an audio indicator that can warn the patient when the remaining battery charge is inadequate to complete a therapy session.

In yet another aspect, the invention features a controller for delivering electrical control signals to a mouthpiece during a non-invasive neuromodulation therapy session. The controller includes an elongated u-shaped element configured to rest upon a patient's shoulders. The controller also includes an electronic receptacle located at a terminus of the three-dimensional u-shaped element for connecting to a cable. The controller also includes a microcontroller located within the three-dimensional u-shaped element, the microprocessor configured to send electrical control signals to the mouthpiece, the electrical control signals determining an amplitude and duration of electrical signals delivered to the patient's tongue.

In some embodiments, the controller also includes an accelerometer for measuring an activity level of the patient and a data logger for logging information related to the activity level of the patient. In some embodiments, the controller also includes an audio alarm for indicating at least one of the end of a therapy session, a low electrical signal delivered to the patient's tongue, activation/deactivation of the controller, or pausing of the electrical signals delivered to the patient's tongue. In some embodiments, the controller also includes a power switch for activating and deactivating the controller and one or more intensity buttons for controlling the intensity of electrical signals delivered to the mouthpiece by the controller. In some embodiments, the controller also includes a display for presenting information and receiving input from the patient. In some embodiments, the controller also includes a battery for providing a current to the mouthpiece. In some embodiments, the controller also includes a motor for causing the u-shaped element to vibrate. In some embodiments, the controller also includes at least one printed circuit board for mounting electrical isolation circuitry, battery management circuitry, and a microcontroller, at least one printed circuit board for mounting a play button, a pause button, and the electronic receptacle, and at least one circuit board for mounting one or more intensity buttons. In some embodiments, the controller also includes circuitry for sensing a current delivered to a patient's tongue via the mouthpiece. In some embodiments, the controller also includes a cable forming an integral portion of the mouthpiece.

In yet another aspect, the invention features a controller for delivering electrical control signals to a mouthpiece during a non-invasive neuromodulation therapy session. The controller includes a coextensively dimensioned element configured to rest in proximity to a patient's face. The controller also includes a receptacle located at a central portion of a first surface of the coextensively dimensioned element, the receptacle providing an electrical and mechanical connection to the mouthpiece. The controller also includes a display located on a second surface of the coextensively dimensioned element, the display providing visual indications to the patient. The controller also includes a microcontroller located within the coextensively dimensioned element, the microcontroller configured to send electrical control signals to the mouthpiece, the electrical control signals determining an amplitude and duration of electrical signals delivered to the patient's tongue.

In some embodiments, the controller also includes an accelerometer for measuring an activity level of the patient and a data logger for logging the activity level of the patient, transmissions to or from the controller, the intensity of electrical signals delivered to the mouthpiece, and information received circuitry configured to determine if the patient's tongue is in contact with the mouthpiece. In some embodiments, the controller also includes an audio alarm for indicating at least one of the end of a therapy session, a low electrical signal delivered to the patient's tongue, activation/deactivation of the controller, or pausing of the electrical signals delivered to the patient's tongue. In some embodiments, the controller also includes a power switch for activating and deactivating the controller and one or more intensity buttons located on a third surface of the coextensively dimensioned element, the intensity buttons controlling the intensity of electrical signals delivered to the mouthpiece by the controller. In some embodiments, the controller also includes a display for presenting information and receiving input from the patient. In some embodiments, the controller also includes a battery for providing a current to the mouthpiece. In some embodiments, the controller also includes a motor for causing the coextensively dimensioned element to vibrate. In some embodiments, the controller also includes at least one printed circuit board for mounting electrical isolation circuitry, battery management circuitry, and a microcontroller, at least one printed circuit board for mounting a play button and a pause button, at least one printed circuit board for mounting the circuitry associated with the receptacle, and at least one circuit board for mounting one or more intensity buttons. In some embodiments, the controller also includes circuitry for sensing a current delivered to a patient's tongue via the mouthpiece.

In yet another aspect, the invention features a method for providing non-invasive neurorehabilitation of a patient. The method includes connecting a mouthpiece to a controller. The method also includes transmitting a numeric sequence generated by a first processor within the controller to the mouthpiece. The method also includes generating a first hash code by a second processor within the mouthpiece, the first hash code based on the received numeric sequence and a shared secret key stored in memory within the mouthpiece. The method also includes transmitting the first hash code from the mouthpiece to the controller. The method also includes generating a second hash code by the first processor within the controller, the second hash code based on the random number and the shared secret key. The method also includes comparing, by the first processor, the first hash code with the second hash code. The method also includes enabling electrical communication between the mouthpiece and the controller only if the first hash code matches the second hash code. The method also includes contacting the mouthpiece with the patient's intraoral cavity. The method also includes delivering neurostimulation to the patient's intraoral cavity, the neurostimulation being delivered by the controller via the mouthpiece.

In some embodiments, the method also includes connecting the mouthpiece to the controller via a cable. In some embodiments, the method also includes providing power to the controller. In some embodiments, the method also includes delivering electrical neurostimulation via an electrode array to the patient's intraoral cavity.

In yet another aspect, the invention features a method for providing non-invasive neurorehabilitation of a patient via a controller and a mouthpiece. The method includes connecting the mouthpiece to the controller. The method also includes generating a first hash code based on a unique serial number and a shared secret key. The method also includes storing the unique serial number and the first hash code in memory located in the mouthpiece. The method also includes transmitting the first hash code and the unique serial number from the mouthpiece to the controller. The method also includes generating a second hash code in a first processor in the controller, the second hash code based on the unique serial number and the shared secret key. The method also includes permitting electrical communication between the mouthpiece and the controller only if the first hash code matches the second hash code. The method also includes contacting the mouthpiece with the patient's intraoral cavity. The method also includes delivering neurostimulation to the patient's intraoral cavity, the neurostimulation being delivered by the controller via the mouthpiece.

In some embodiments, the method also includes connecting the mouthpiece to the controller via a cable. In some embodiments, the method also includes providing power to the controller. In some embodiments, the method also includes delivering electrical neurostimulation via an electrode array to the patient's intraoral cavity. In some embodiments, the first hash code is an SHA-256 hash code.

In yet another aspect, the invention features a mouthpiece for providing neurorehabilitation to a patient, the mouthpiece receiving electrical neurostimulation signals from a controller and selectively delivering the received electrical neurostimulation signals to the patient. The mouthpiece includes an elongated housing having an anterior region and a posterior region, the elongated housing having a non-planar exterior top surface. The mouthpiece also includes a printed circuit board mounted to a bottom portion of the elongated housing, the printed circuit board having a plurality of electrodes for delivering subcutaneous local electrical stimulation to the patient's tongue. The mouthpiece also includes control circuitry mounted within a top portion of the elongated housing for controlling electrical signals delivered to the electrodes. The mouthpiece also includes a memory mounted within a top portion of the elongated housing. The mouthpiece also includes a processor mounted within the top portion of the elongated housing, the processor configured to (i) receive a numeric sequence from the controller, (ii) generate a first hash code based on the received numeric sequence and a shared secret key stored in the memory, (iii) transmit the first hash code to the controller, (iv) receive communications from the controller only if a second hash code based on the numeric sequence and the shared secret key generated at the controller matches the first hash code.

In yet another aspect, the invention features a mouthpiece for providing neurorehabilitation to a patient, the mouthpiece receiving electrical neurostimulation signals from a controller and selectively delivering the received electrical neurostimulation signals to the patient. The mouthpiece includes an elongated housing having an anterior region and a posterior region, the elongated housing having a non-planar exterior top surface. The mouthpiece also includes a printed circuit board mounted to a bottom portion of the elongated housing, the printed circuit board having a plurality of electrodes for delivering subcutaneous local electrical stimulation to the patient's tongue. The mouthpiece also includes control circuitry mounted within a top portion of the elongated housing for controlling electrical signals delivered to the electrodes. The mouthpiece also includes a memory mounted within the top portion of the elongated housing. The mouthpiece also includes a processor mounted within the top portion of the elongated housing, the processor configured to (i) store a first hash code and a unique serial number, the first hash code based on the unique serial number and a shared secret key (ii) transmit the first hash code and the unique serial number to the controller, (iv) receive communications from the controller only if a second hash code based on the unique serial number and the shared secret key generated at the controller matches the first hash code. In some embodiments, the first hash code is an SHA-256 hash code.

In yet another aspect, the invention features a system for providing non-invasive neuromodulation to a patient. The system includes a mouthpiece and a controller. The mouthpiece includes an elongated housing having an anterior region and a posterior region, the elongated housing having a non-planar exterior top surface. The mouthpiece also includes a printed circuit board mounted to a bottom portion of the elongated housing, the printed circuit board having a plurality of electrodes for delivering subcutaneous local electrical stimulation to the patient's tongue. The mouthpiece also includes control circuitry mounted within a top portion of the elongated housing for controlling electrical signals delivered to the electrodes. The mouthpiece also includes a cable with a first end attached to the anterior portion of the elongated housing and having a connector at a second end for connecting to a controller, the cable delivering electrical current to the electrodes via the control circuitry. The controller includes an elongated u-shaped element having first and second arms that separate an anterior portion from a posterior portion, the anterior portion of the elongated u-shaped element located at a first distance from one of the arms and having a first mass, and the posterior portion of the elongated u-shaped element located at a second distance from the other of the arms and having a second mass, the product of the first mass and the first distance being larger than the product of the second mass and the second distance. The controller also includes an electronic receptacle located at the anterior portion of the u-shaped element connecting to the cable. The controller also includes a microcontroller located within the three-dimensional u-shaped element, the microcontroller configured to send electrical control signals to the mouthpiece, the electrical control signals determining an amplitude and duration of electrical signals delivered to the patient's tongue.

In some embodiments, the width of the elongated-u-shaped element corresponds to approximately the $60^{th}$ percentile of adult male neck widths. In some embodiments, the length of the elongated-u-shaped element is approximately 200 mm. In some embodiments, the width of the elongated-u-shaped element is approximately 120 mm. In some embodiments, the anterior portion includes a first portion having a first width of approximately 35 mm and a second portion having a second width of approximately 35 mm, the first portion being attached to the first arm, and the second portion being attached to the second arm. In some embodiments, the first mass is greater than the second mass. In some embodiments, the first mass is smaller than the second mass. In some embodiments, the first and second distances are determined based on a portion of the arms configured to contact a patient's shoulders. In some embodiments, the arms have a radius of curvature in the range of 20-30 cm in a sagittal plane of the patient to cause the controller to substantially conform to a patient's shoulders. In some embodiments, the width of the elongated u-shaped element is between 60% and 80% of the length of the elongated u-shaped element. In some embodiments, the width of the elongated u-shaped element is approximately 60% of the length of the elongated u-shaped element. In some embodiments, an interior contour of the posterior portion has a radius of curvature in the range of 20-60 mm in a transverse plane of the patient. In some embodiments, an interior contour of the posterior portion has a radius of curvature of approximately 40 mm in a transverse plane of the patient. In some embodiments, an exterior contour of the posterior portion has a radius of curvature in the range of 10-40 mm in a transverse plane of the patient. In some embodiments, an exterior contour of the posterior portion has a radius of curvature of approximately 25 mm in a transverse plane of the patient. In some embodiments, a contour of the first and second arms has a radius of curvature in the range of 330-430 mm in a transverse plane of the patient. In some embodiments, a contour of the first and second arms has a radius of curvature of approximately 380 mm in a transverse plane of the patient. In some embodiments, the anterior portion includes an opening having a width in the range of 30-60 mm. In some embodiments, the anterior portion includes an opening having a width of approximately 45 mm. In some embodiments, the system includes an accelerometer for measuring an activity level of the patient. In some embodiments, the system includes a data logger for logging information related to the activity level of the patient. In some embodiments, the system includes tongue sense circuitry for determining if a patient's tongue is in contact with the plurality of electrodes located on the bottom portion of the mouthpiece. In some embodiments, the system includes a clock for determining a total time of usage of the mouthpiece. In some embodiments, the system includes a battery for providing a current to the mouthpiece. In some embodiments, the system includes an optical indicator that indicates a power level of the battery. In some embodiments, the system includes an audio indicator that can warn the patient when the remaining battery charge is inadequate to complete a therapy session.

In yet another aspect, the invention features a system for providing non-invasive neuromodulation to a patient. The system includes a mouthpiece and a controller. The mouthpiece includes an elongated housing having an anterior region and a posterior region, the elongated housing having a non-planar exterior top surface. The mouthpiece also includes a printed circuit board mounted to the elongated housing, the printed circuit board having a plurality of electrodes for delivering subcutaneous local electrical stimulation to the patient's tongue. The mouthpiece also includes control circuitry mounted within the elongated housing for controlling electrical signals delivered to the electrodes. The mouthpiece also includes a first communication module delivering electrical current to the electrodes via the control circuitry. The controller includes an elongated u-shaped element having first and second arms that separate an anterior portion from a posterior portion, the anterior portion of the elongated u-shaped element located at a first distance from one of the arms and having a first mass, and the posterior portion of the elongated u-shaped element located at a second distance from the other of the arms and having a second mass, the product of the first mass and the first distance being larger than the product of the second mass and the second distance. The controller also includes a second communication module within the housing coupled to and in communication with the first communication module. The controller also includes a microcontroller located within the housing and configured to exchange electrical signals with the mouthpiece, the electrical signals determining an amplitude and duration of electrostimulation energy pulses delivered to the patient's tongue.

In some embodiments, the system includes an accelerometer for measuring an activity level of the patient. In some embodiments, the system includes a data logger for logging information related to the activity level of the patient. In some embodiments, the system includes tongue sense circuitry for determining if a patient's tongue is in contact with the plurality of electrodes located on the bottom portion of the mouthpiece. In some embodiments, the system includes a clock for determining a total time of usage of the mouthpiece. In some embodiments, the system includes a battery for providing a current to the mouthpiece. In some embodiments, the system includes an optical indicator that indicates a power level of the battery. In some embodiments, the system includes an audio indicator that can warn the patient when the remaining battery charge is inadequate to complete a therapy session. In some embodiments, the width of the elongated-u-shaped element corresponds to approximately the $60^{th}$ percentile of adult male neck widths. In some embodiments, the length of the elongated-u-shaped element is approximately 200 mm. In some embodiments, the width of the elongated-u-shaped element is approximately 120 mm. In some embodiments, the anterior portion includes a first portion having a first width of approximately 35 mm and a second portion having a second width of approximately 35 mm, the first portion being attached to the first arm, and the second portion being attached to the second arm. In some embodiments, the first mass is greater than the second mass. In some embodiments, the first mass is smaller than the second mass. In some embodiments, the first and second distances are determined based on the location of the arms configured to contact a patient's shoulders. In some embodiments, the first and second distances are determined based on a portion of the arms configured to contact a patient's shoulders. In some embodiments, the arms have a radius of curvature of in the range of 20 to 30 cm in a sagittal plane of the patient to cause the controller to substantially conform to a patient's shoulders. In some embodiments, the width of the elongated u-shaped element is between 60% and 80% of the length of the elongated u-shaped element. In some embodiments, the width of the elongated u-shaped element is approximately 60% of the length of the elongated u-shaped element. In some embodiments, an interior contour of the posterior portion has a radius of curvature in the range of 20-60 mm in a transverse plane of the patient. In some embodiments, an interior contour of the posterior portion has a radius of curvature of approximately 40 mm in a transverse plane of the patient. In some embodiments, an exterior contour of the posterior portion has a radius of curvature in the range of 10-40 mm in a transverse plane of the patient. In some embodiments, an exterior contour of the posterior portion has a radius of curvature of approximately 25 mm in a transverse plane of the patient. In some embodiments, a contour of the first and second arms has a radius of curvature in the range of 330-430 mm in a transverse plane of the patient. In some embodiments, a contour of the first and second arms has a radius of curvature of approximately 380 mm in a transverse plane of the patient. In some embodiments, the anterior portion includes an opening having a width in the range of 30-60 mm. In some embodiments, the anterior portion includes an opening having a width of approximately 45 mm.

As used herein, the terms "approximately," "roughly," and "substantially" mean±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DETAILED DESCRIPTION

Figure 1:
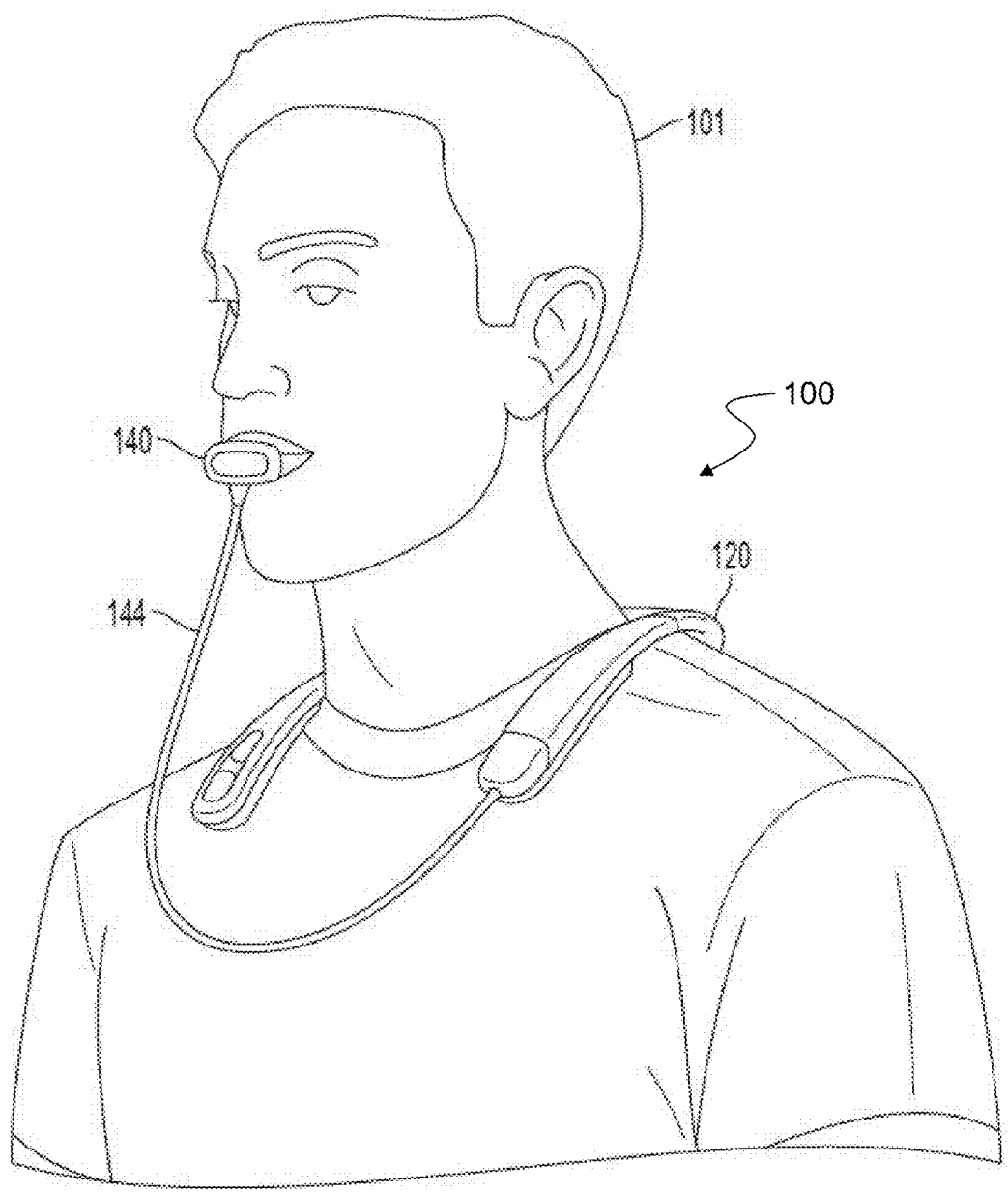
FIG. 1 is a drawing of a patient engaged in a non-invasive neurostimulation therapy session according to an illustrative embodiment of the invention.

FIG. 1 shows a patient 101 undergoing non-invasive neuromodulation therapy (NINM) using a neurostimulation system 100. During a therapy session, the neurostimulation system 100 non-invasively stimulates various nerves located within the patient's oral cavity, including at least one of the trigeminal and facial nerves. In combination with the NINM, the patient engages in an exercise or other activity specifically designed to assist in the neurorehabilitation of the patient. For example, the patient can perform a physical therapy routine (e.g., moving an affected limb, or walking on a treadmill) engage in a mental therapy (e.g., meditation or breathing exercises), or a cognitive exercise (e.g., computer assisted memory exercises) during the application of NINM. The combination of NINM with an appropriately chosen exercise or activity has been shown to be useful in treating a range of maladies including, for example, traumatic brain injury, stroke (TBI), multiple sclerosis (MS), balance, gait, vestibular disorders, visual deficiencies, tremor, headache, migraines, neuropathic pain, hearing loss, speech recognition, auditory problems, speech therapy, cerebral palsy, blood pressure, relaxation, and heart rate. For example, a useful non-invasive neuromodulation (NINM) therapy routine has been recently developed as described in U.S. Pat. No. 8,849,407, the entirety of which is incorporated herein by reference.

Figure 2A:
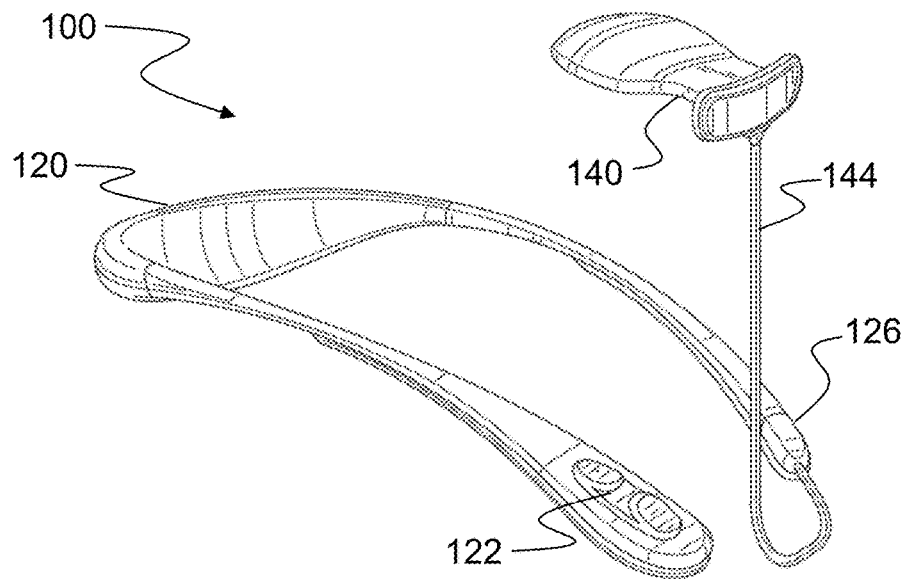
FIGS. 2A and 2B are diagrams showing a neurostimulation system according to an illustrative embodiment of the invention.
Figure 2B:
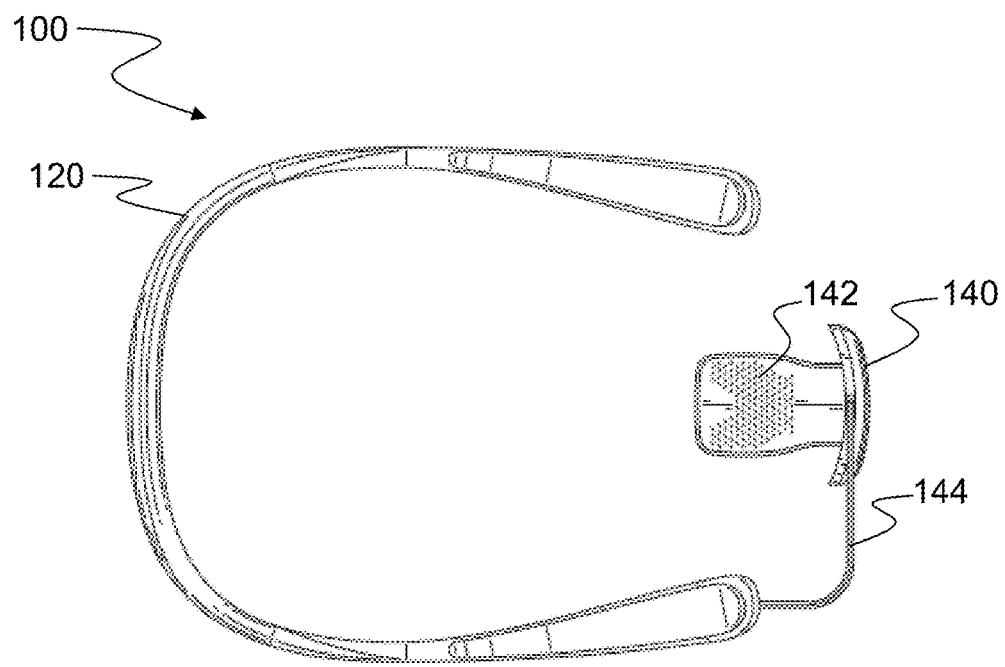

FIGS. 2A and 2B show a non-invasive neurostimulation system 100. The non-invasive neurostimulation system 100 includes a controller 120 and a mouthpiece 140. The controller 120 includes a receptacle 126 and pushbuttons 122. The mouthpiece 140 includes an electrode array 142 and a cable 144. The cable 144 connects to the receptacle 126, providing an electrical connection between the mouthpiece 140 and the controller 120. In some embodiments, the controller 120 includes a cable. In some embodiments, the mouthpiece 140 and the controller 120 are connected wirelessly (e.g., without the use of a cable). During operation, a patient activates the neurostimulation system 100 by actuating one of the pushbuttons 122. In some embodiments, the neurostimulation system 100 periodically transmits electrical pulses to determine if the electrode array 142 is in contact with the patient's tongue and automatically activates based on the determination. After activation, the patient can start an NINM treatment session, stop the NINM treatment session, or pause the NINM treatment session by pressing one of the pushbuttons 122. In some embodiments, the neurostimulation system 100 periodically transmits electrical pulses to determine if the electrode array 142 is in contact with the patient's tongue and automatically pauses the NINM treatment session based on the determination. During an NINM treatment session, the patient engages in an exercise or other activity designed to facilitate neurorehabilitation. For example, during an NINM treatment session, the patient can engage in a physical exercise, a mental exercise, or a cognitive exercise. In some embodiments, the controller 120 has pushbuttons on both arms. In some embodiments, a mobile device can be used in conjunction with the controller 120 and the mouthpiece 140. The mobile device can include a software application that allows a user to activate the neurostimulation system 100 and start or stop an NINM treatment session by for example, pressing a button on the mobile device, or speaking a command into the mobile device. The mobile device can obtain patient information and treatment session information before, during, or after an NINM treatment session. In some embodiments, the controller 120 includes a secure cryptoprocessor that holds a secret key, to be described in more detail below in connection with FIGS. 9A and 9B. The secure cryptoprocessor is in communication with a microcontroller. The secure cryptoprocessor can be tamper proof. For example, if outer portions of the cryptoprocessor are removed in an attempt to access the secret key, the cryptoprocessor erases all memory, preventing unauthorized access of the secret key.

Figure 2C:
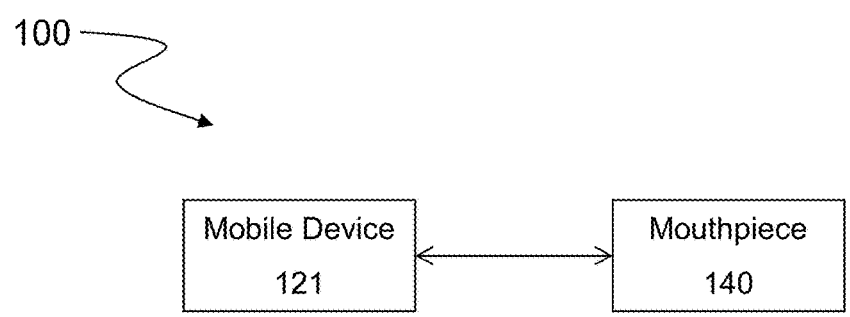
FIG. 2C is a diagram showing a neurostimulation system according to an illustrative embodiment of the invention.

FIG. 2C shows a non-invasive neurostimulation system 100. As shown, a mobile device 121 is in communication with a mouthpiece 140. More specifically, the mobile device 121 includes a processor running a software application that facilitates communications with the mouthpiece 140. The mobile device 121 can be, for example, a mobile phone, a portable digital assistant (PDA), or a laptop. The mobile device 121 can communicate with the mouthpiece 140 by a wireless or wired connection. During operation, a patient activates the neurostimulation system 100 via the mobile device 121. After activation, the patient can start an NINM treatment session, stop the NINM treatment session, or pause the NINM treatment session by manipulating the mobile device 121. During an NINM treatment session, the patient engages in an exercise or activity designed to provide neurorehabilitation. For example, during an NINM treatment session, the patient can engage in a physical exercise, a mental exercise, or a cognitive exercise.

Figure 3A:
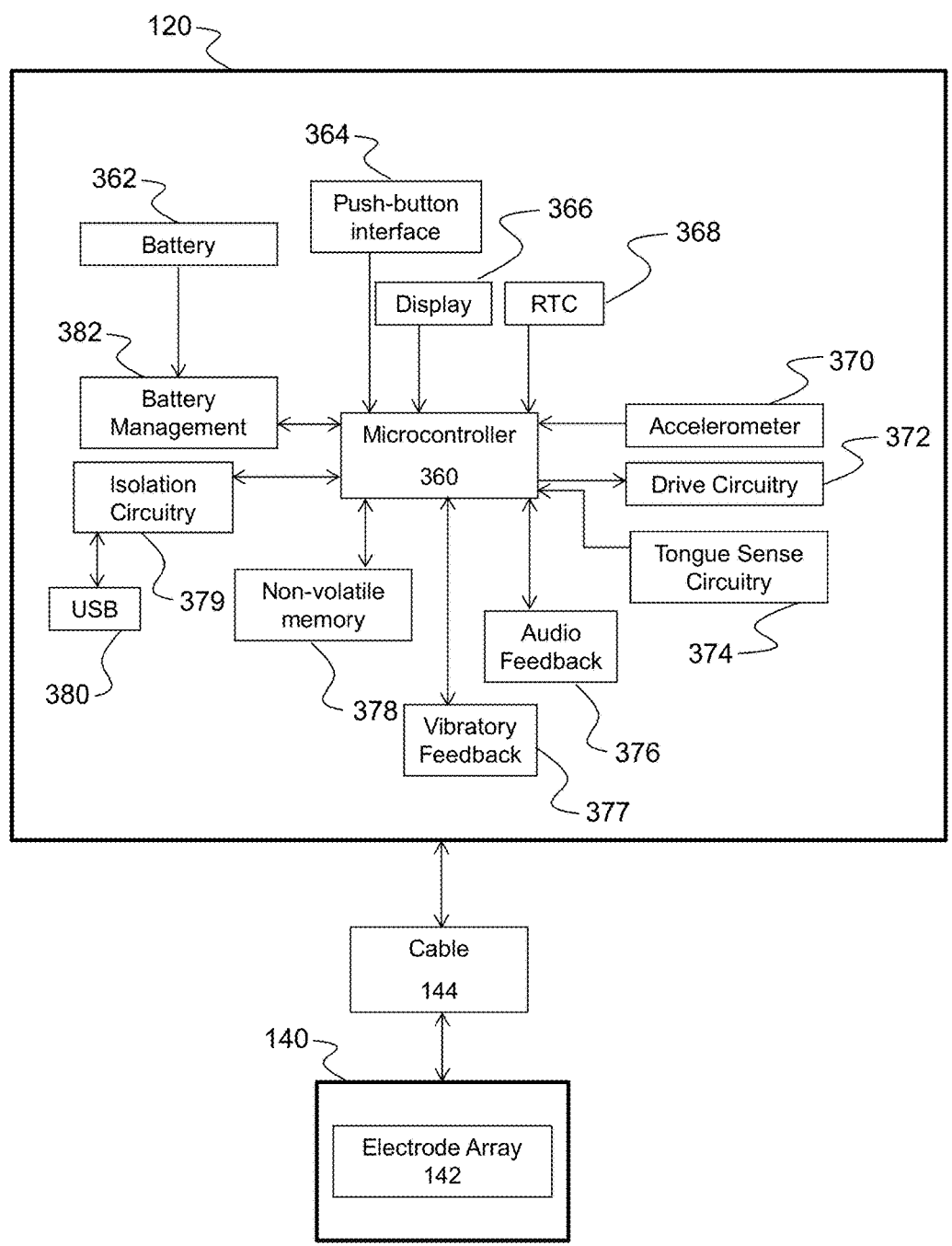
FIG. 3A is a diagram showing a more detailed view of the neurostimulation system depicted in FIGS. 2A and 2B.

FIG. 3A shows the internal circuitry housed within the controller 120. The circuitry includes a microcontroller 360, isolation circuitry 379, a universal serial bus (USB) connection 380, a battery management controller 382, a battery 362, a push-button interface 364, a display 366, a real time clock 368, an accelerometer 370, drive circuitry 372, tongue sense circuitry 374, audio feedback circuitry 376, vibratory feedback circuitry 377, and a non-volatile memory 378. The drive circuitry 372 includes a multiplexor, and an array of resistors to control voltages delivered to the electrode array 142. The microcontroller 360 is in electrical communication with each of the components shown in FIG. 3A. The isolation circuitry 379 provides electrical isolation between the USB connection 380 and all other components included in the controller 120. Additionally, the circuitry shown in FIG. 3A is in communication with the mouthpiece 140 via the external cable 144. During operation, the microcontroller 360 receives electrical power from battery 362 and can store and retrieve information from the non-volatile memory 378. The battery can be charged via the USB connection 380. The battery management circuitry controls the charging of the battery 362. A patient can interact with the controller 120 via the push-button interface 122 that converts the patient's pressing of a button (e.g. an info button, a power button, an intensity-up button, an intensity-down button, and a start/stop button) into an electrical signal that is transmitted to the microcontroller 360. For example, a therapy session can be started when the patient presses a start/stop button after powering on the controller 120. During the therapy session, the drive circuitry 372 provides an electrical signal to the mouthpiece 140 via the cable 144. The electrical signal is communicated to the patient's intraoral cavity via the electrode array 142. The accelerometer 370 can be used to provide information about the patient's motion during the therapy session. Information provided by the accelerometer 370 can be stored in the non-volatile memory 378 at a coarse or detailed level. For example, a therapy session aggregate motion index can be stored based on the number of instances where acceleration rises above a predefined threshold, with or without low pass filtering. Alternatively, acceleration readings could be stored at a predefined sampling interval. The information provided by the accelerometer 370 can be used to determine if the patient is engaged in a physical activity. Based on the information received from the accelerometer 370, the microcontroller 360 can determine an activity level of the patient during a therapy session. For example, if the patient engages in a physical activity for 30 minutes during a therapy session, the accelerometer 370 can periodically communicate (e.g. once every second) to the microcontroller 360 that the sensed motion is larger than a predetermined threshold (e.g. greater than 1 m/s$^2$). In some embodiments, the accelerometer data is stored in the non-volatile memory 378 during the therapy session and transmitted to the mobile device 121 after the therapy session has ended. After the therapy session has ended, the microcontroller 360 can record the amount of time during the therapy session in which the patient was active. In some embodiments, the recorded information can include other data about the therapy session (e.g., the date and time of the session start, the average intensity of electrical neurostimulation delivered to the patient during the session, the average activity level of the patient during the session, the total session time the mouthpiece has been in the patient's mouth, the total session pause time, the number of session shorting events, and/or the length of the session or the type of exercise or activity performed during the therapy session) and can be transmitted to a mobile device. A session shorting event can occur if the current transmitted from the drive circuitry to the electrode array 142 exceeds a predetermined threshold or if the charge transmitted from the drive circuitry to the electrode array exceeds a predetermined threshold over a predetermined time interval. After a session shorting event has occurred, the patient must manually press a pushbutton to resume the therapy session. The real time clock (RTC) 368 provides time and date information to the microcontroller 360. In some embodiments, the controller 120 is authorized by a physician for a predetermined period of time (e.g., two weeks). The RTC 368 periodically communicates date and time information to the microcontroller 360. In some embodiments, the RTC 368 is integrated with the microcontroller. In some embodiments, the RTC 368 is powered by the battery 362, and upon failure of the battery 362, the RTC 368 is powered by a backup battery. After the predetermined period of time has elapsed, the controller 120 can no longer initiate the delivery of electrical signals to the mouthpiece 140 and the patient must visit the physician to reauthorize use of the controller 120. The display 366 displays information received by the microcontroller 360 to the patient. For example, the display 366 can display the time of day, therapy information, battery information, time remaining in a therapy session, error information, and the status of the controller 120. The audio feedback circuitry 376 and vibratory feedback circuitry 377 can give feedback to a user when the device changes state. For example, when a therapy session begins, the audio feedback circuitry 376 and the vibratory feedback circuitry 377 can provide auditory and/or vibratory cues to the patient, notifying the patient that the therapy session has been initiated. Other possible state changes that may trigger audio and/or vibratory cues include pausing a therapy session, resuming a therapy session, the end of a timed session, canceling a timed session, or error messaging. In some embodiments, a clinician can turn off one or more of the auditory or vibratory cues to tailor the feedback to an individual patient's needs. The tongue sense circuitry 374 measures the current passing from the drive circuitry to the electrode array 142. Upon sensing a current above a predetermined threshold, the tongue sense circuitry 374 presents a high digital signal to the microcontroller 360, indicating that the tongue is in contact with the electrode array 142. If the current is below the predetermined threshold, the tongue sense circuitry 374 presents a low digital signal to the microcontroller 360, indicating that the tongue is not in contact or is in partial contact with the electrode array 142. The indications received from the tongue sense circuitry 374 can be stored in the non-volatile memory 378. In some embodiments, the display 366 can be an organic light emitting diode (OLED) display. In some embodiments, the display 366 can be a liquid crystal display (LCD). In some embodiments, a display 366 is not included with the controller 120. In some embodiments, neither the controller 120 nor the mouthpiece 140 includes a cable, and the controller 120 communicates wirelessly with the mouthpiece 140. In some embodiments, neither the controller 120 nor the mouthpiece 140 includes an accelerometer. In some embodiments, the drive circuitry 372 is located within the mouthpiece. In some embodiments, a portion of the drive circuitry 372 is located within the mouthpiece 140 and a portion of the drive circuitry 372 is located within the controller 120. In some embodiments, neither the controller 120 nor the mouthpiece 140 includes tongue sense circuitry 374. In some embodiments, the mouthpiece 140 includes a microcontroller and a multiplexer.

Figure 3B:
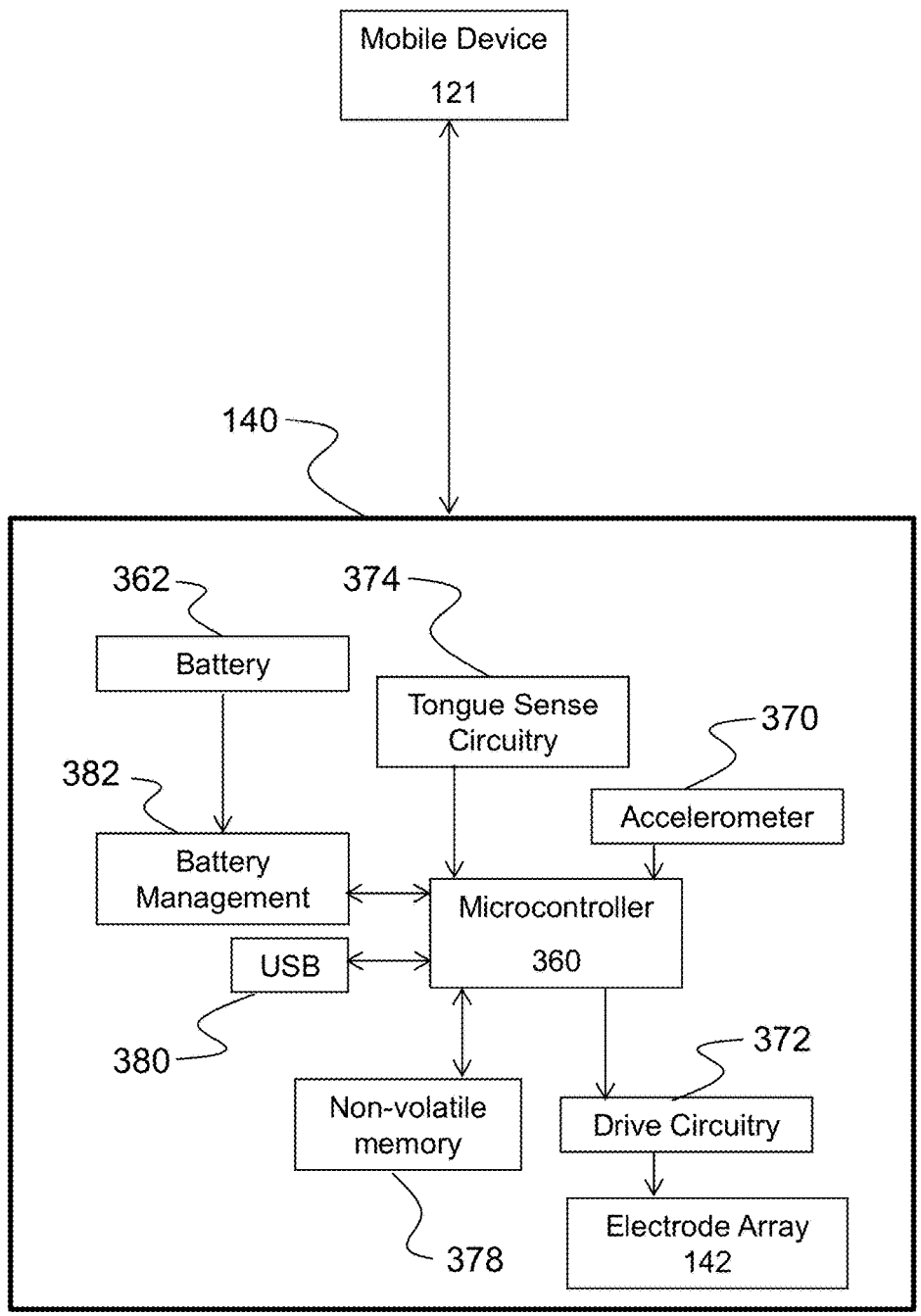
FIG. 3B is a diagram showing a more detailed view of the neurostimulation system depicted in FIG. 2C.

FIG. 3B shows a more detailed view of FIG. 2C. The mouthpiece 140 includes a battery 362, tongue sense circuitry 374, an accelerometer 370, a microcontroller 360, drive circuitry 372, a non-volatile memory 378, a universal serial bus controller (USB) 380, and battery management circuitry 382. During operation, the microcontroller receives electrical power from battery 362 and can store and retrieve information from the non-volatile memory 378. The battery can be charged via the USB connection 380. The battery management circuitry 382 controls the charging of the battery 362. A patient can interact with the mouthpiece 140 via the mobile device 121. The mobile device 121 includes an application (e.g. software running on a processor) that allows the patient to control the mouthpiece 140. For example, the application can include an info button, a power button an intensity-up button, an intensity-down button, and a start/stop button that are presented to the user visually via the mobile device 121. When the patient presses a button presented by the application running on the mobile device 121, a signal is transmitted to the microcontroller 360 housed within the mouthpiece 140. For example, a therapy session can be started when the patient presses a start/stop button on the mobile device 121. During the therapy session, the drive circuitry 372 provides an electrical signal to an electrode array 142 located on the mouthpiece 140. The accelerometer 370 can be used to provide information about the patient's motion during the therapy session. The information provided by the accelerometer 370 can be used to determine if the patient is engaged in a physical activity. Based on the information received from the accelerometer 370, the microcontroller 360 can determine an activity level of the patient during a therapy session. For example, if the patient engages in a physical activity for 30 minutes during a therapy session, the accelerometer 370 can periodically communicate (e.g. once every second) to the microcontroller 360 that the sensed motion is larger than a predetermined threshold (e.g. greater than 1 m/s$^2$). After the therapy session has ended, the microcontroller 360 can record the amount of time during the therapy session in which the patient was active. In some embodiments, the accelerometer 370 is located within the mobile device 121 and the mobile device 121 determines an activity level of a patient during the therapy session based on information received from the accelerometer 370. The mobile device can then record the amount of time during the therapy session in which the patient was active. The mobile device 121 includes a real time clock (RTC) 368 that provides time and date information to the microcontroller 360. In some embodiments, the mouthpiece 140 is authorized by a physician for a predetermined period of time (e.g., two weeks). After the predetermined period of time has elapsed, the mouthpiece 140 can no longer deliver electrical signals to the patient via the electrode array 142 and the patient must visit the physician to reauthorize use of the mouthpiece 140. In some embodiments, the mouthpiece 140 includes pushbuttons (e.g., an on/off button) and a patient can manually operate the mouthpiece 140 via the pushbuttons. After a therapy session, the mouthpiece 140 can transmit information about the therapy session to a mobile device. In some embodiments, the mouthpiece 140 does not include a USB controller 380 and instead communicates only via wireless communications with the controller.

Figure 3C:
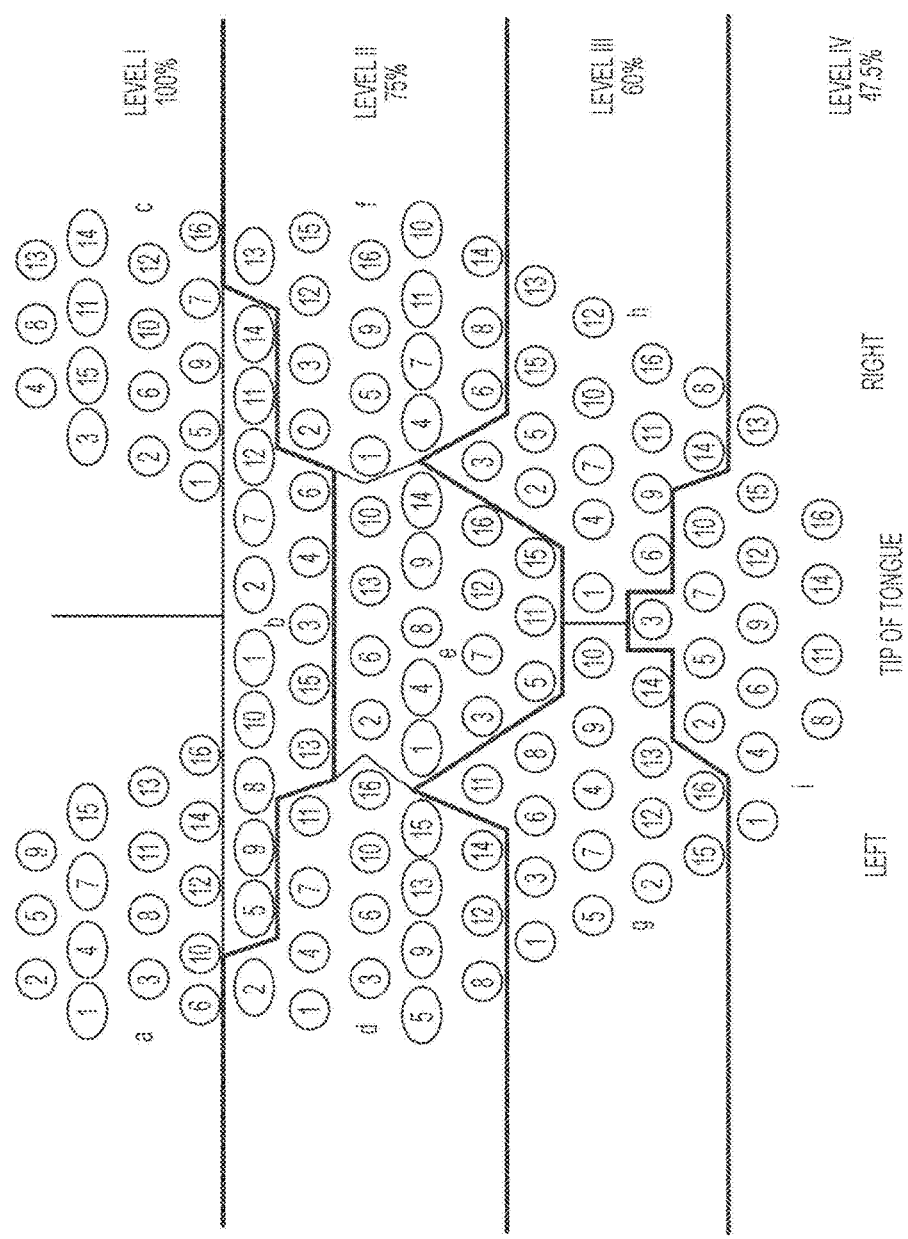
FIG. 3C is a diagram showing a more detailed view of an electrode array.

FIG. 3C shows a more detailed view of the electrode array 142. The electrode array 142 can be separated into 9 groups of electrodes, labelled a-i, with each group having 16 electrodes, except group b which has 15 electrodes. Each electrode within the group corresponds to one of 16 electrical channels. During operation, the drive circuitry can deliver a sequence of electrical pulses to the electrode array 142 to provide neurostimulation of at least one of the patient's trigeminal or facial nerve. The electrical pulse amplitude delivered to each group of electrodes can be larger near a posterior portion of the tongue and smaller at an anterior portion of the tongue. For example, the pulse amplitude of electrical signals delivered to groups a-c can be 19 volts or 100% of a maximum value, the pulse amplitude of electrical signals delivered to groups d-f can be 14.25 volts or 75% of the maximum value, the pulse amplitude of electrical signals delivered to groups g-h can be 11.4 volts or 60% of the maximum value, and the pulse amplitude of electrical signals delivered to group i can be 9.025 volts or 47.5% of the maximum value. In some embodiments, the maximum voltage is in the range of 0 to 40 volts. The pulses delivered to the patient by the electrode array 142 can be random or repeating. The location of pulses can be varied across the electrode array 142 such that different electrodes are active at different times, and the duration and/or intensity of pulses may vary from electrode. For oral tissue stimulation, currents of 0.5-50 mA and voltages of 1-40 volts can be used. In some embodiments, transient currents can be larger than 50 mA. The stimulus waveform may have a variety of time-dependent forms, and for cutaneous electrical stimulation, pulse trains and bursts of pulses can be used. Where continuously supplied, pulses may be 1-500 microseconds long and repeat at rates from 1-1000 pulses/second. Where supplied in bursts, pulses may be grouped into bursts of 1-100 pulses/burst, with a burst rate of 1-100 bursts/second.

Figure 3D:
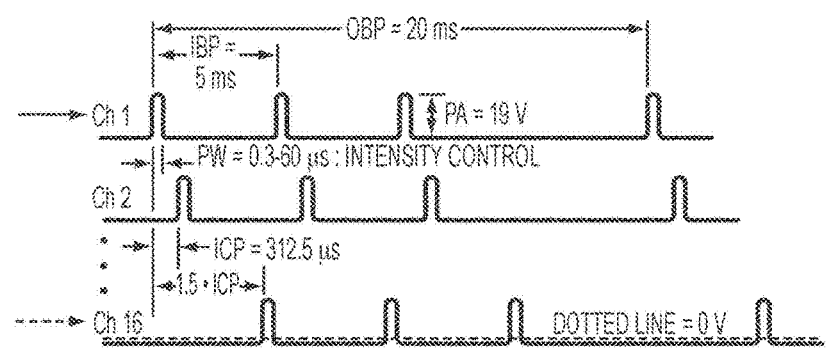
FIG. 3D is a graph showing an exemplary sequence of pulses for effecting neurostimulation of a patient.

In some embodiments, pulsed waveforms are delivered to the electrode array 142. FIG. 3D shows an exemplary sequence of pulses that can be delivered to the electrode array 142 by the drive circuitry 372. A burst of three pulses, each spaced apart by 5 ms is delivered to each of the 16 channels. The pulses in neighboring channels are offset from one another by 312.5 μs. The burst of pulses repeats every 20 ms. The width of each pulse can be varied from 0.3-60 μs to control an intensity of neurostimulation (e.g., a pulse having a width of 0.3 μs will cause a smaller amount of neurostimulation than a pulse having a width of 60 μs).

Figure 4A:
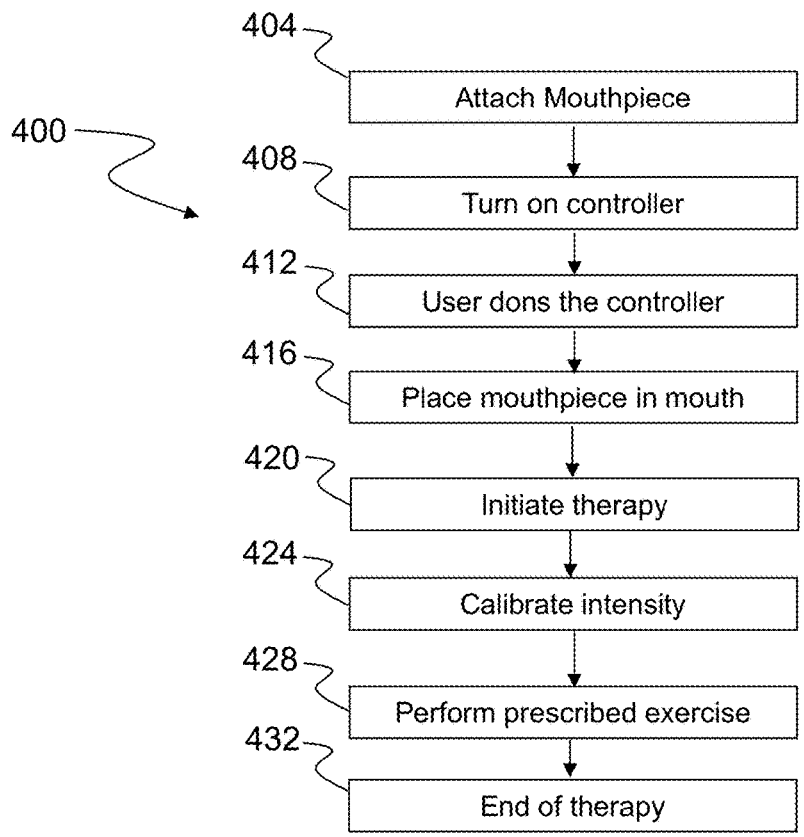
FIG. 4A is a flow chart illustrating a method in accordance with one embodiment for operating a neurostimulation system.

FIG. 4A shows a method of operation 400 of a controller 120 as described in FIGS. 2A, 2B and 3A. A patient attaches a mouthpiece 140 to a controller 120 (step 404). The patient turns on the controller 120 (step 408) using, for example, a power button. The patient places the controller 120 around his/her neck (step 412) as shown in FIG. 1B. The patient places a mouthpiece 140 in his/her mouth (step 416). The patient initiates a therapy session by pressing a start/stop button (step 420). During the therapy session, the controller 120 delivers electrical signals to the mouthpiece 140. The patient calibrates the intensity of the electrical signals (step 424). The patient raises the intensity of the electrical signals delivered to the mouthpiece by pressing an intensity-up button until the neurostimulation is above the patient's sensitivity level. The patient presses an intensity-down button until the neurostimulation is comfortable and non-painful. After the calibration step, the patient performs a prescribed exercise (step 428). The exercise can be cognitive, mental, or physical. In some embodiments, physical exercise includes the patient attempting to maintain a normal posture or gait, the patient moving his/her limbs, or the patient undergoing speech exercises. Cognitive exercises can include "brain training" exercises, typically computerized, that are designed to require the use of attention span, memory, or reading comprehension. Mental exercises can include visualization exercises, meditation, relaxation techniques, and progressive exposure to "triggers" for compulsive behaviors.

In some embodiments, the patient can rest for a period of time during the therapy session (e.g. the patient can rest for 2 minutes during a 30 minute therapy session). After a predetermined period of time (for example, thirty minutes) has elapsed, the therapy session ends (step 432) and the controller 120 stops delivering electrical signals to the mouthpiece 140. In some embodiments, the intensity of electrical signals increases from zero to the last use level selected by the patient over a time duration in the range of 1-5 seconds after the patient starts a therapy session by pressing the start/stop button. In some embodiments, the intensity of electrical signals is set to a fraction of the last use level selected by the patient (e.g. ¾ of the last level selected) after the patient starts a therapy session by pressing the start/stop button. In some embodiments, the intensity of electrical signals increases from zero to a fraction of the last use level selected by the patient (e.g. ¾ of the last level selected) over a time duration in the range of 1-5 seconds after the patient starts a therapy session by pressing the start/stop button. In some embodiments, the intensity of electrical signals increases instantaneously from zero to the last use level selected by the patient after the patient starts a therapy session by pressing the start/stop button.

In some embodiments, the mouthpiece 140 is connected to the controller 120 after the controller 120 is turned on. In some embodiments, the mouthpiece 140 is connected to the controller 120 after the controller 120 is donned by the patient. In some embodiments, the patient calibrates the intensity of the electrical signals before initiating a therapy session. In some embodiments, a patient performs an initial calibration of the intensity of electrical signals in the presence of a clinician and does not calibrate the intensity of the electrical signals during subsequent treatments performed in the absence of a clinician.

Figure 4B:
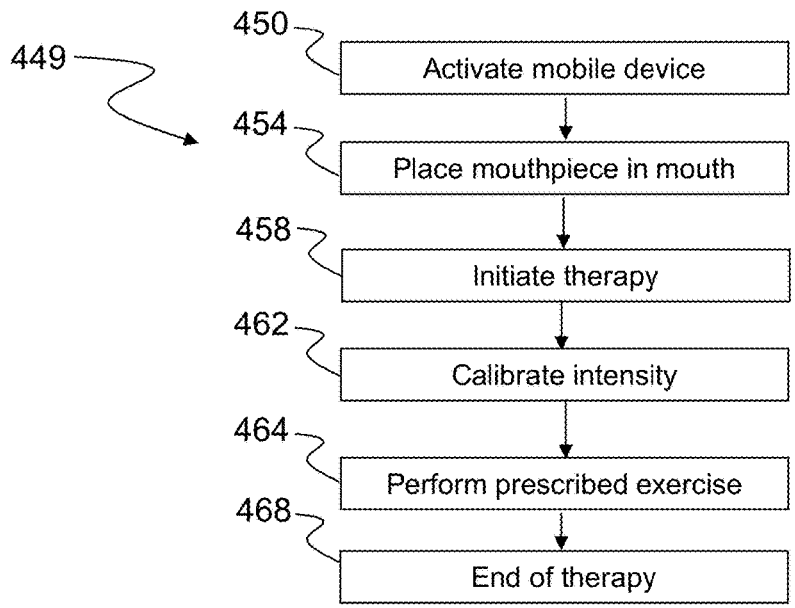
FIG. 4B is a flow chart illustrating a method in accordance with one embodiment for operating a neurostimulation system.

FIG. 4B shows a method of operation 449 of the non-invasive neurostimulation system 100 described in FIGS. 2C and 3B. A patient activates a mobile device 121 (step 450). The patient places a mouthpiece 140 in his/her mouth (step 454). The patient initiates a therapy session by pressing a start/stop button within an application running on the mobile device 121 (step 458). During the therapy session, circuitry within the mouthpiece 140 delivers electrical signals to an electrode array 142 located on the mouthpiece 140. The patient calibrates the intensity of the electrical signals (step 462). The patient first raises the intensity of the electrical signals delivered to the mouthpiece 140 by pressing an intensity-up button located within an application running on the mobile device 121 until the neurostimulation is above the patient's sensitivity level. The patient presses an intensity-down button running within an application on the mobile device 121 until the neurostimulation is comfortable and non-painful. After the calibration step, the patient performs a prescribed exercise (step 464). The exercise can be cognitive, mental, or physical. In some embodiments, the patient can rest for a period of time during the therapy session (e.g. the patient can rest for 5 minutes during a 30 minute therapy session). After a predetermined period of time (for example, thirty minutes) has elapsed, the therapy session ends (step 468) and the circuitry located within the mouthpiece 140 stops delivering electrical signals to the electrode array 142. In some embodiments, the calibration of the intensity of the electrical signals takes place before the patient initiates a therapy session.

Figure 5A:
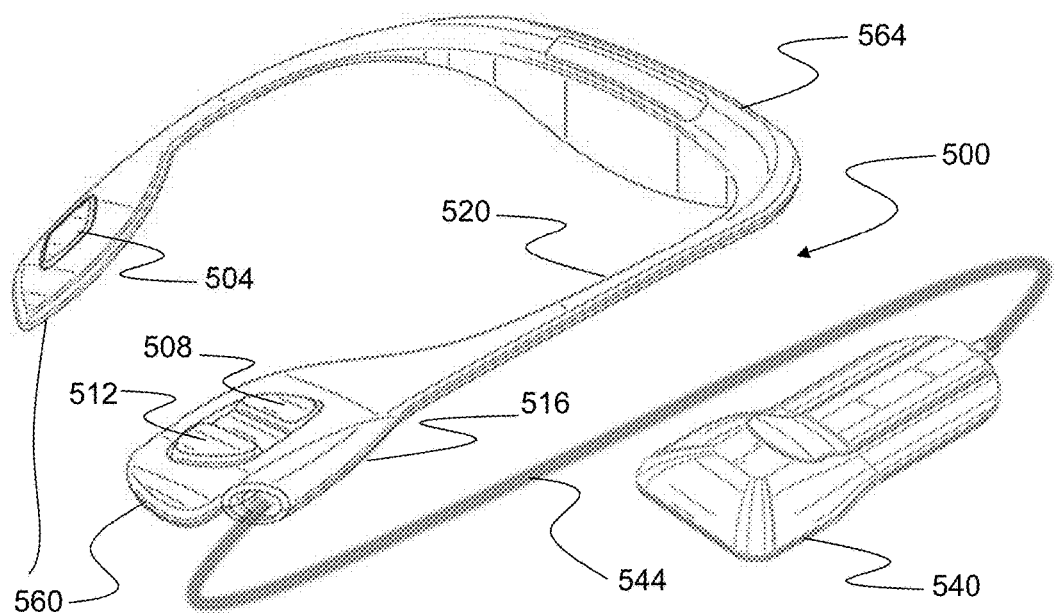
FIG. 5A is a diagram showing a neurostimulation system according to an illustrative embodiment of the invention.
Figure 5B:
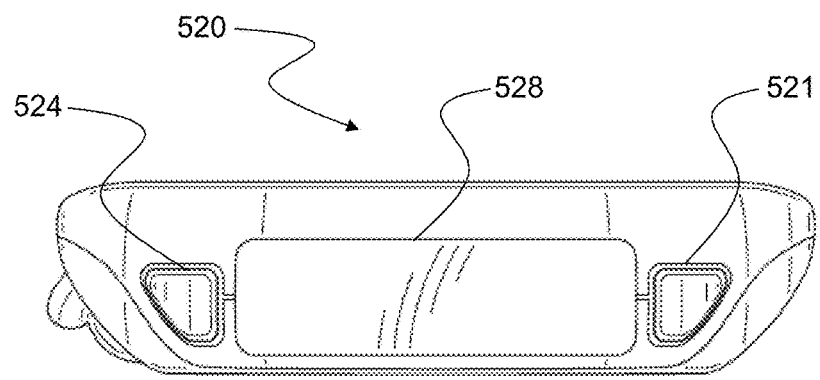
FIG. 5B is a diagram showing a controller according to an illustrative embodiment of the invention.

FIG. 5A shows a neurostimulation system 500 and FIG. 5B shows a back view of a controller 520. The neurostimulation system 500 includes a controller 520 and a mouthpiece 540 connected via a cable 544. The mouthpiece 540 includes an electrode array on a bottom portion thereof. The controller 520 includes an anterior portion 560 and a posterior portion 564. The controller 520 also includes a mouthpiece port 516, an intensity-up button 508, an intensity-down button 512, a power button 521, an info button 524, a start/stop button 504 and a display 528. The mouthpiece 540 is in electrical communication with the controller 520 via the cable 544. In some embodiments, the power button 521 includes a light emitting diode (LED) indicator. In some embodiments, the port 516 is located on the mouthpiece 540 instead of the controller 520 and the cable 544 is permanently attached to the controller 520. In some embodiments the port is a universal serial bus (USB) port and/or a charging port.

Figure 5C:
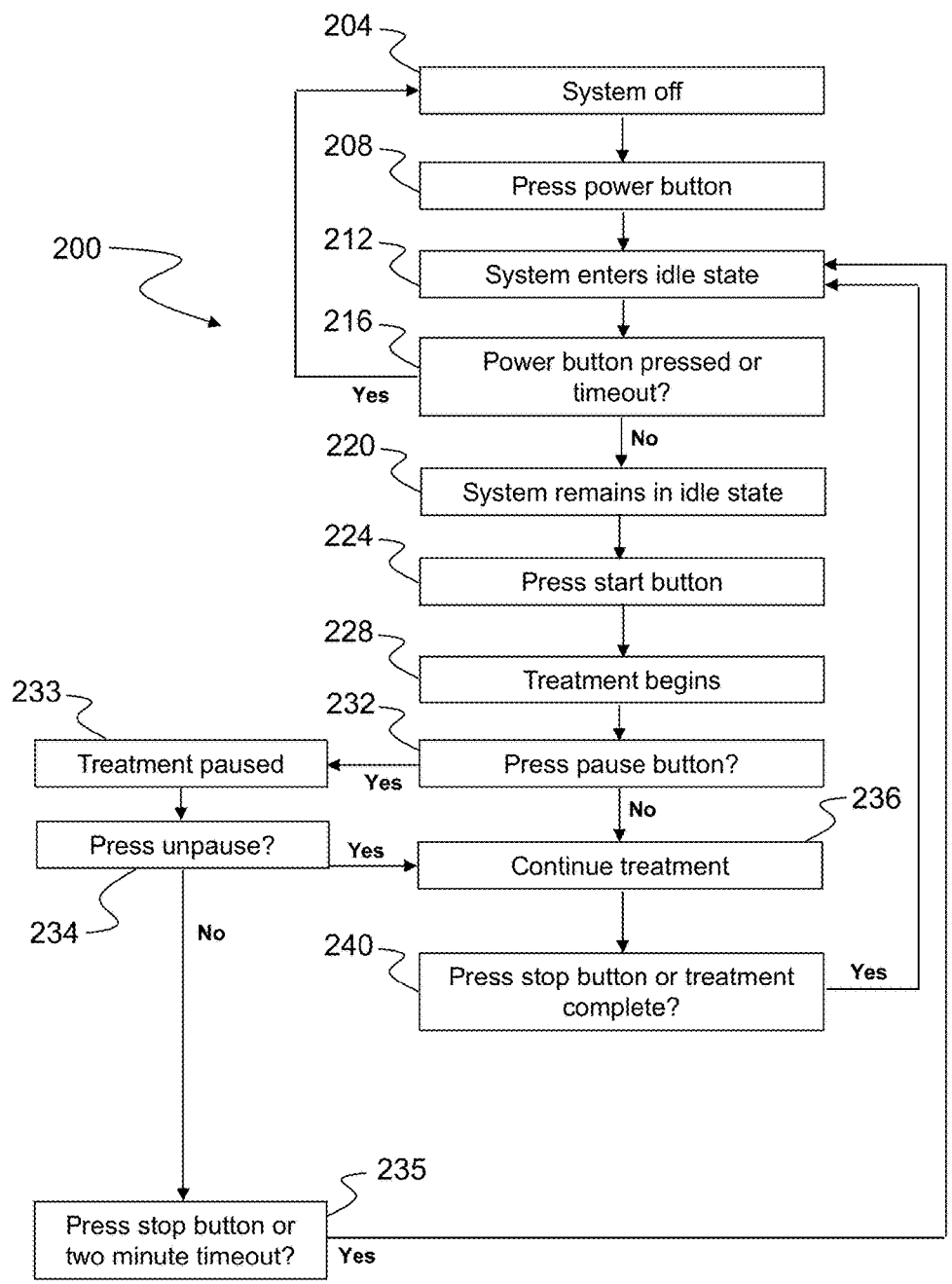
FIG. 5C is a flow chart illustrating a method in accordance with one embodiment for operating a neurostimulation system.

FIG. 5C describes a method 200 of operating the neurostimulation system 500 shown in FIGS. 5A and 5B. A patient activates the neurostimulation system 500 by pressing a power button 521 (step 208). After activation, the neurostimulation system 500 enters an idle state (step 212). While in the idle state, non-invasive neurostimulation is not delivered to the patient. If the neurostimulation system 500 remains in the idle state for a predetermined time period, the neurostimulation system 500 can shut down or enter a power-saving state (e.g., after idling for 10 minutes). Additionally, if the power button 521 is pressed while in the idle state, the neurostimulation system 500 shuts down. If the patient presses a start button (step 224), an NINM therapy session begins and non-invasive neurostimulation generated by the controller 520 is delivered to the patient's oral cavity via the mouthpiece 540 for a predetermined period of time. In some embodiments, the neurostimulation system 500 enters an intensity adjustment state when the patient presses a start button (step 224). The patient then raises the intensity of the electrical signals delivered to the mouthpiece by pressing the intensity-up button 508 until the neurostimulation is above the patient's sensitivity level. The patient presses the intensity-down button 512 until the neurostimulation is comfortable and non-painful. After the intensity adjustment is completed, the patient presses the start button again to begin an NINM therapy session. In one embodiment, the predetermined period of time can be in the user-selectable range of 20-30 minutes. Additionally, the patient performs a physical, cognitive, or mental exercise during the NINM therapy session. The physical, cognitive, or mental exercise is performed simultaneously with the delivery of electrical signals from the controller 520 to the mouthpiece 540. If the patient presses a pause button (step 232) while neurostimulation is being delivered, the therapy session is paused (step 233) and the neurostimulation system 500 ceases to deliver non-invasive neurostimulation to the patient's oral cavity. In some embodiments, if the neurostimulation system 500 loses contact with the patient's oral cavity (e.g. determined by tongue sensing circuitry), the therapy session is paused. If the patient presses unpause (step 234), the treatment is resumed and non-invasive neurostimulation is again delivered to the patient's intraoral cavity. If the patient presses the stop button while the neurostimulation system 500 is paused, or if there is no patient input for more than a predetermined time, for example, two minutes (step 235) after the patient has pressed the pause button, the neurostimulation system 500 enters an idle state (step 212) and a "treatment ended due to pause timeout" message is presented by the display 528. If the patient presses the stop button (step 240) while neurostimulation is being delivered, the neurostimulation system 500 enters an idle state (step 212) and a "treatment ended due to session stop" message is presented by the display 528. Alternatively, if the neurostimulation system 500 delivers neurostimulation to the patient for the full predetermined period of time at step 240, the system enters an idle state at step 212 and a "full session completed" message is presented by the display 528.

While the system is in the idle state at step 212, a number of conditions can prevent the patient from initiating a therapy session. For example, if there is not enough charge remaining in the battery to complete at least one NINM therapy session, the controller 520 can block the patient from initiating the therapy session and a "low battery" message will be presented on the display 528. In some embodiments, the controller can emit an audible sound to alert the patient that there is not enough charge remaining in the battery to complete at least one NINM therapy session. Additionally, if the mouthpiece 540 is not attached to the controller 520, the controller 520 can block the patient from initiating a therapy session and a "no mouthpiece" message is presented on the display 528.

In some embodiments, the neurostimulation system 500 delivers neurostimulation for a limited number of hours per day. For example, the neurostimulation system 500 can be configured to stop delivering neurostimulation after 200 minutes of use in a single day. In the idle state at step 212, if the daily limit has been exceeded, the controller 520 can block the patient from initiating a therapy session and a "daily limit reached" message is presented by the display 528. The patient can begin treatment the next day (i.e., after midnight), when the daily limit is reset.

In some embodiments, the neurostimulation system 500 delivers neurostimulation for a limited number of weeks. In the idle state at step 212, if the calendar limit has been exceeded, the controller 520 can block the patient from initiating a therapy session and a "calendar limit reached" message is presented by the display 528. For example, the neurostimulation system 500 can be configured to stop delivering neurostimulation 1-14 weeks after the patient receives the neurostimulation system 500 from a physician. To re-enable the neurostimulation system 500 after the calendar limit has been exceeded, the patient is required to visit a physician or a clinician. In some embodiments, a "calendar limit approaching" message is presented by the display 528, warning the patient that the calendar limit will be reached soon (e.g. in two weeks). The "calendar limit approaching" message can be beneficial to patients by allowing them to schedule appointments with their clinicians prior to the calendar limit being reached.

In some embodiments, the mouthpiece 540 can become damaged over time and require replacement. For example, the patient's bites down on the mouthpiece 540 during each therapy session, slowly causing the surface of the mouthpiece to be damaged. This damage can cause the mouthpiece 540 to malfunction. The average time to failure can be statistically determined by testing a number of mouthpieces 540 over a number of therapy sessions and examining the mouthpieces for damage at the end of each therapy session. The average time to failure, once determined, can be programmed into the controller 520. During the idle state at step 212, if the average time to failure has been reached, the controller 520 can block the patient from initiating a therapy session and a "mouthpiece expired" message is presented by the display 528. In some embodiments, a message is presented by the display 528, warning the patient that the mouthpiece is set to expire soon. For example, the message presented by the display 528 can be "mouthpiece expires in 14 days."

Figure 9A:
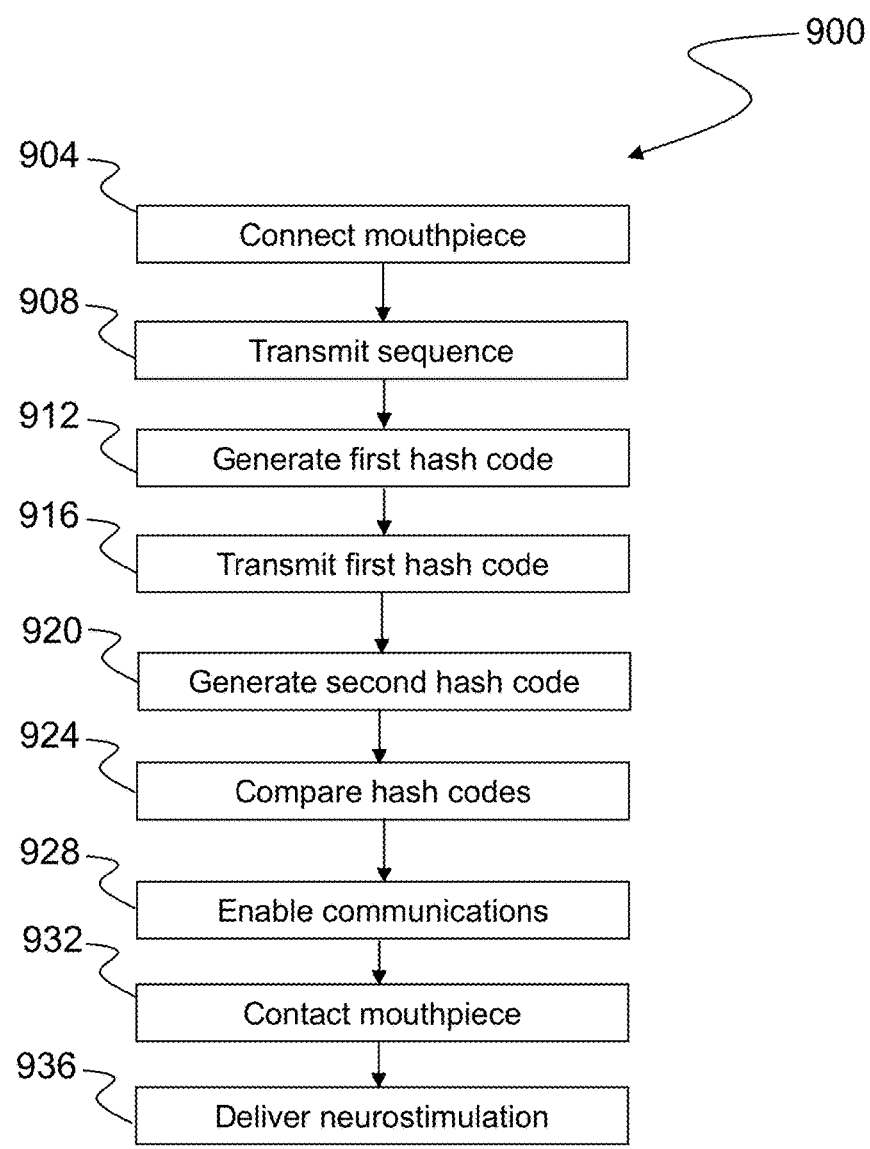
FIG. 9A is a flow chart illustrating a method in accordance with one embodiment for operating a neurostimulation system.
Figure 9B:
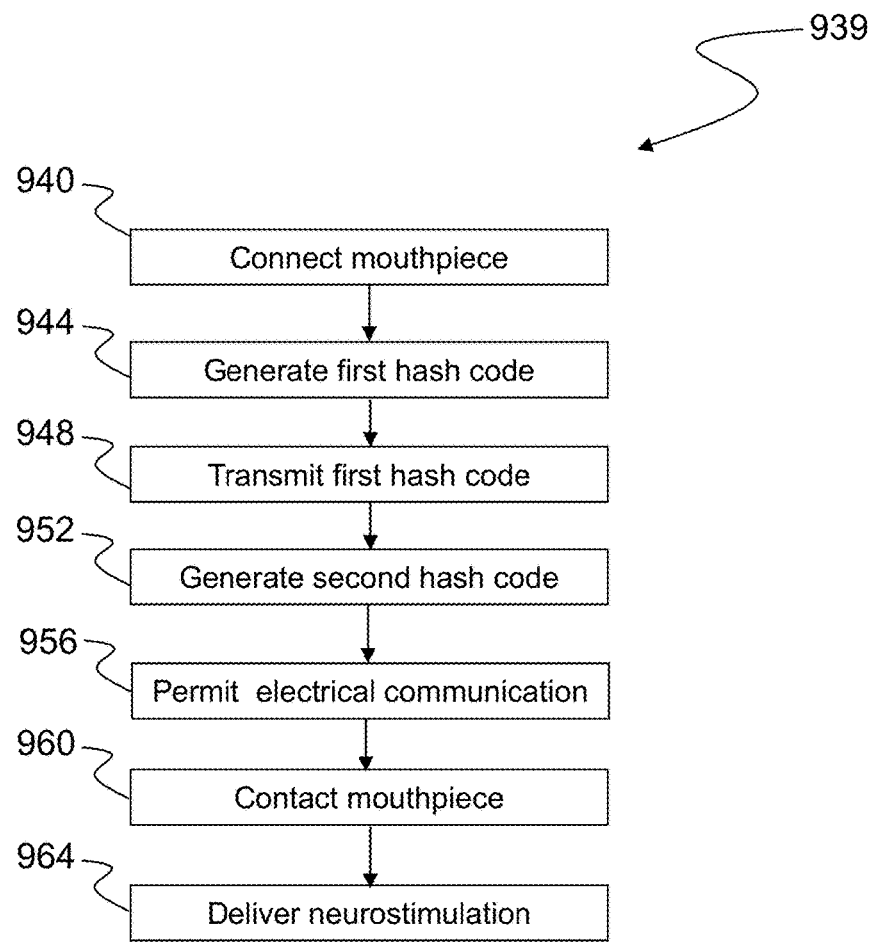
FIG. 9B is a flow chart illustrating a method in accordance with one embodiment for operating a neurostimulation system.
Figure 10A:
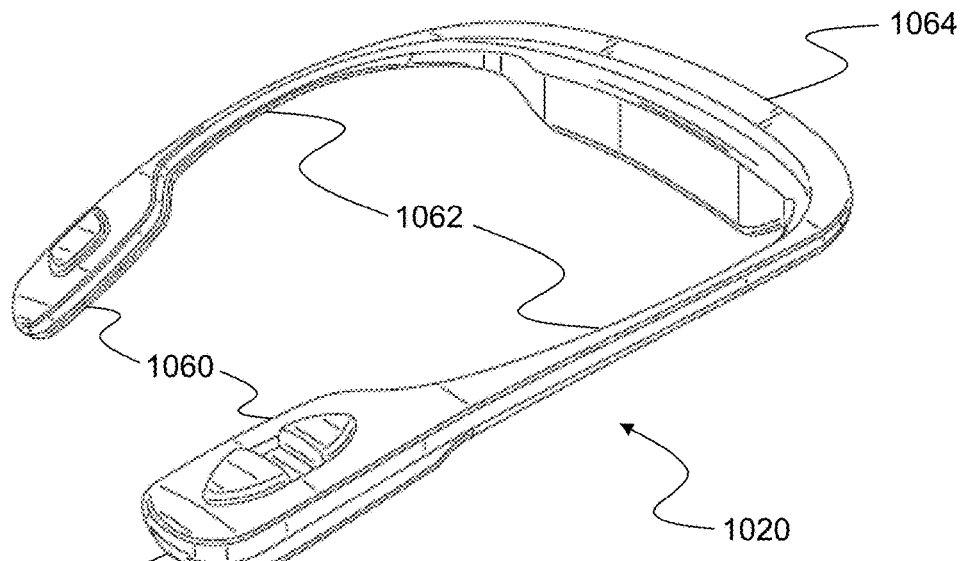
FIGS. 10A-10D are diagrams showing a controller according to an illustrative embodiment of the invention.
Figure 10B:
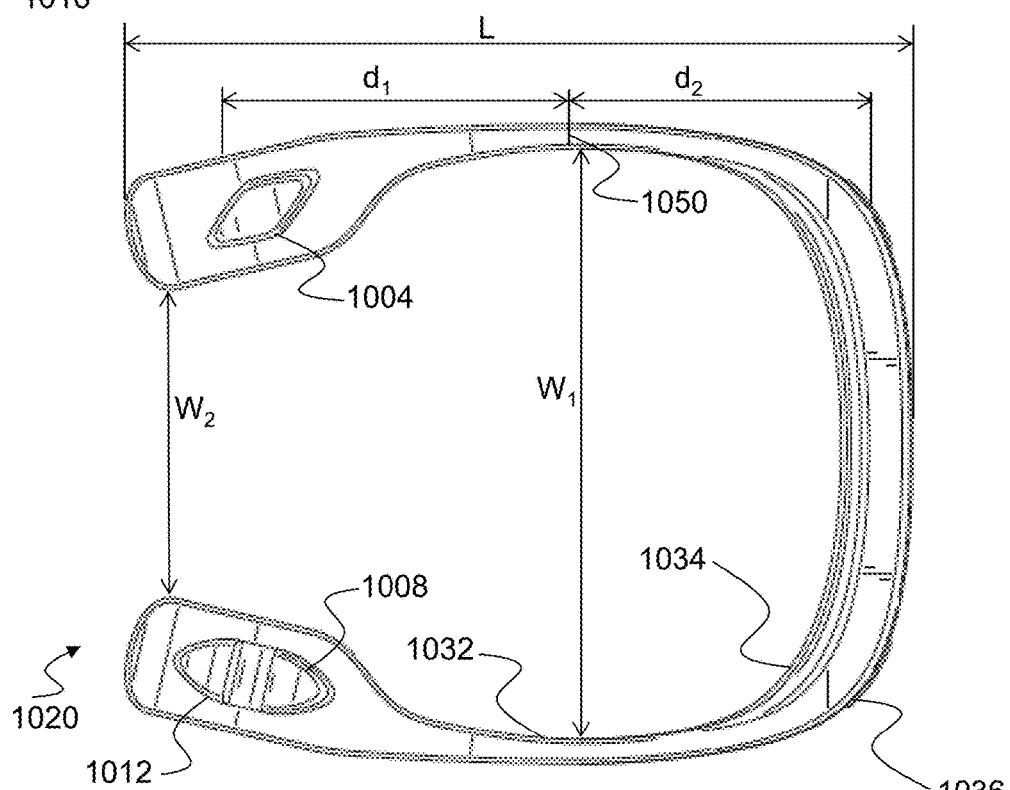
Figure 10C:
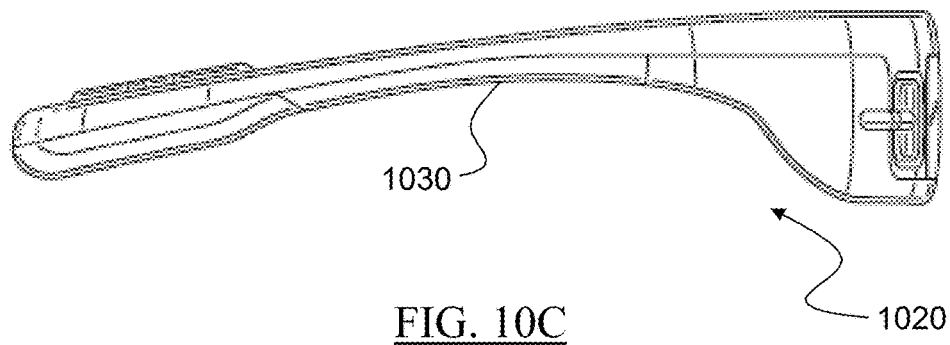
Figure 10D:
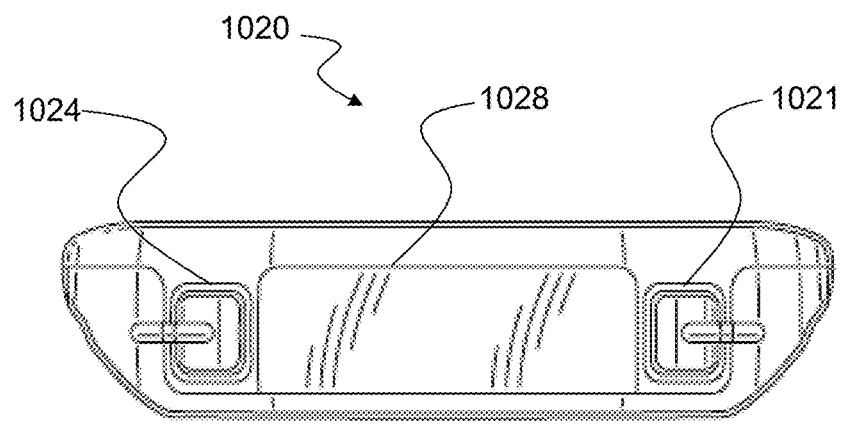

In some embodiments, the display 528 can present an "authentication error" message if a mouthpiece 540 cannot be authenticated, for example as described in FIGS. 9A and 9B. In some embodiments, the neurostimulation system 500 tracks an activity level of a patient. For example, the neurostimulation system 500 can include an accelerometer that detects an activity level of the patient (e.g., at rest, walking, or running). In some embodiments, the activity level can be recorded and stored on an external computer for analysis. For example, the recorded activity level data can be analyzed by a physician to determine an effectiveness of a prescribed treatment plan. In some embodiments, the neurostimulation system 500 sets an intensity level to 75% of the last used intensity level when the treatment begins at step 228. In some embodiments, data including time stamps, intensity levels, data received from the accelerometer, and data received from the tongue sense circuitry can be recorded and stored on an external computer or mobile device for analysis.

In some embodiments, the port 516 can facilitate charging of the neurostimulation system 500. For example, when the port 516 is connected to a charging source, the neurostimulation system 500 enters a charging state. In the charging state, a "Charging" message is presented by the display 528. Additionally, in the charging state, an LED can indicate a remaining battery charge. For example, the LED can emit flashing red light if there is not sufficient battery charge for at least one NINM therapy session. If there is sufficient battery charge remaining to complete at least one NINM therapy session, the LED can emit flashing green. When the battery charging is complete, the LED can emit a solid green light (e.g. a non-flashing green light). While the neurostimulation system 500 is in the charging state, the patient cannot begin an NINM therapy session. When the port is disconnected in the charging state, the neurostimulation system 500 enters an idle state (step 212).

In some embodiments, an LED included with the power button 521 can indicate a remaining battery charge. For example, the LED can emit green light if there is sufficient battery charge remaining to complete two or more NINM therapy sessions. If there is sufficient battery charge remaining to complete one NINM therapy session, the LED can emit yellow light. If there is not enough charge remaining for one NINM therapy session, the LED can emit red light. In some embodiments, the controller 520 includes LEDs for providing visual indication, an audio indicator, or a vibratory indicator that can provide indications to the patient. For example, the LEDs, the audio indicator, and the vibratory indicator can provide an indication to the patient if electrical neurostimulation is being delivered to the mouthpiece 540, if electrical neurostimulation delivery to the mouthpiece 540 has been disabled or cancelled, or if the NINM therapy session has ended. The indications can include a solid or flashing light emitted by the LEDs or a predetermined sound such as a ring, buzz, or chirp emitted by the audio indicator. The vibratory indicator can provide tactile feedback or other vibratory feedback to the patient. In some embodiments, the audio and/or vibratory indicator includes a piezoelectric element or a magnetic buzzer that vibrates and provides a mechanical indication to the patient. In some embodiments, the LEDs and/or the audio indicator provide an indication when an NINM therapy session is 50% complete. In some embodiments, the LEDs and/or the audio indicator provide an indication when any button on the controller 520 is pressed by the patient. In some embodiments, the LEDs and/or the audio indicator provide an indication of the intensity level of the electrical neurostimulation. In some embodiments, the LEDs and/or the audio indicator provide an indication of the remaining NINM therapy session time. In some embodiments, the LEDs and/or the audio indicator provide an indication of the remaining stimulation minutes for the current day (e.g., before a daily limit is reached). In some embodiments, the LEDs and/or the audio indicator provide an indication of the remaining stimulation minutes for the current calendar period (e.g., before a calendar limit is reached). In some embodiments, pressing a start/stop/pause button while neurostimulation is being delivered pauses the therapy session (step 233) and the neurostimulation system 500 ceases to deliver non-invasive neurostimulation to the patient's oral cavity.

Figure 6A:
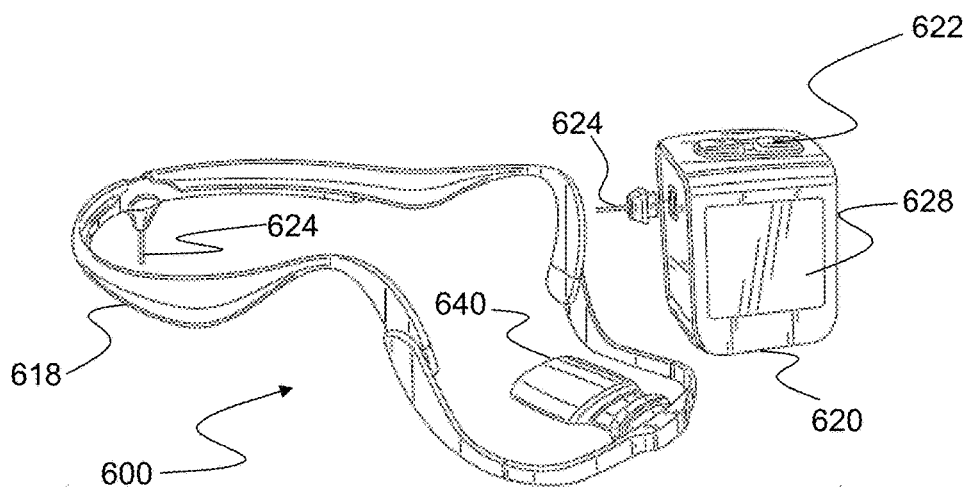
FIGS. 6A and 6B are diagrams showing a neurostimulation system according to an illustrative embodiment of the invention.
Figure 6B:
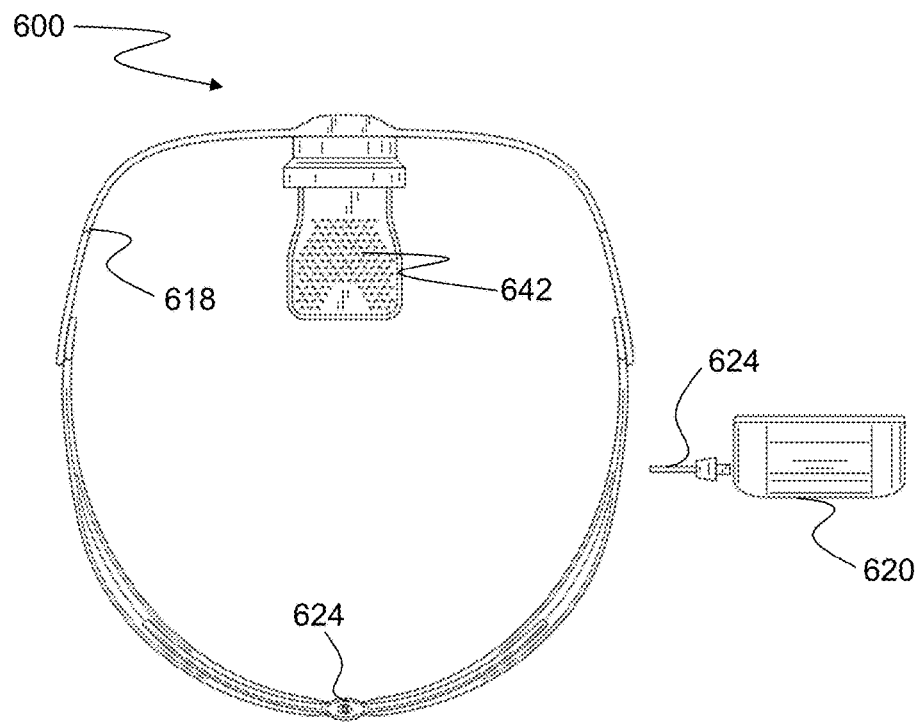

FIGS. 6A and 6B show a non-invasive neurostimulation system 600. The non-invasive neurostimulation system 600 includes headband 618, a controller 620, pushbuttons 622, a display 628, a mouthpiece 640, an electrode array 642, and a cable 624. The controller 620 is in electrical communication with the mouthpiece 640 and the electrode array 642 via the cable 624. During operation, a patient rests the headband 618 along his/her ears and inserts the mouthpiece 640 into his/her mouth. Operation of the non-invasive neurostimulation system 600 is similar to that described above in reference to FIGS. 5A and 5B where similarly referenced elements have the same functionality (e.g. controller 620 has the same functionality as controller 520 etc.). In some embodiments, the headband 618 maintains an orientation of the mouthpiece 640 within the patient's mouth during an NINM therapy session. In some embodiments, the headband 618 maintains the position of the mouthpiece 640 within the patient's mouth, even if the patient is in a horizontal orientation or is upside-down.

Figure 7A:
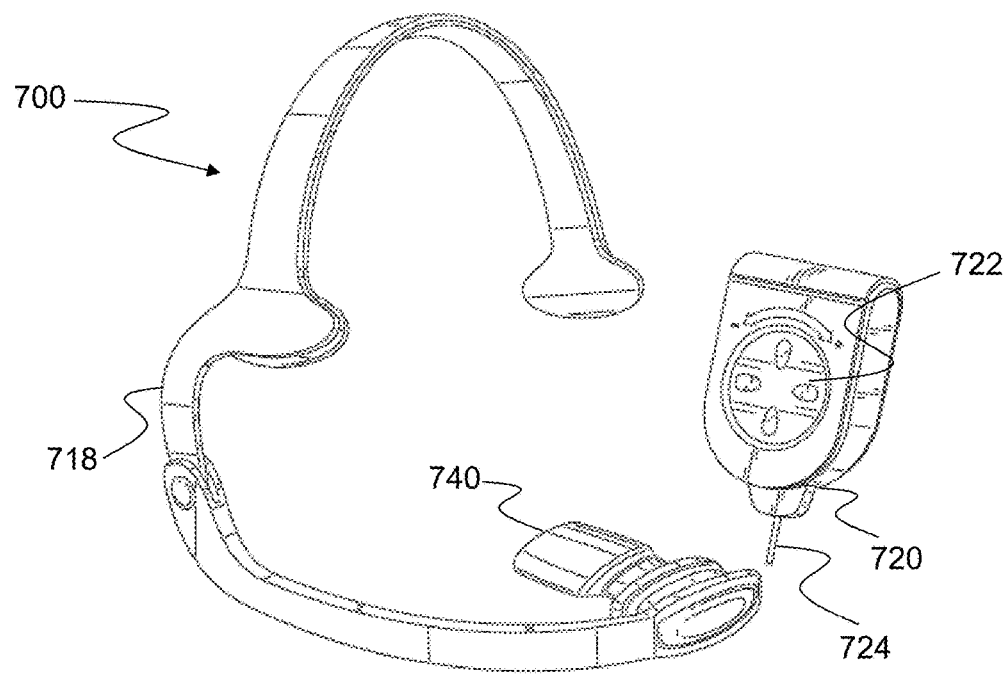
FIGS. 7A and 7B are diagrams showing a neurostimulation system according to an illustrative embodiment of the invention.
Figure 7B:
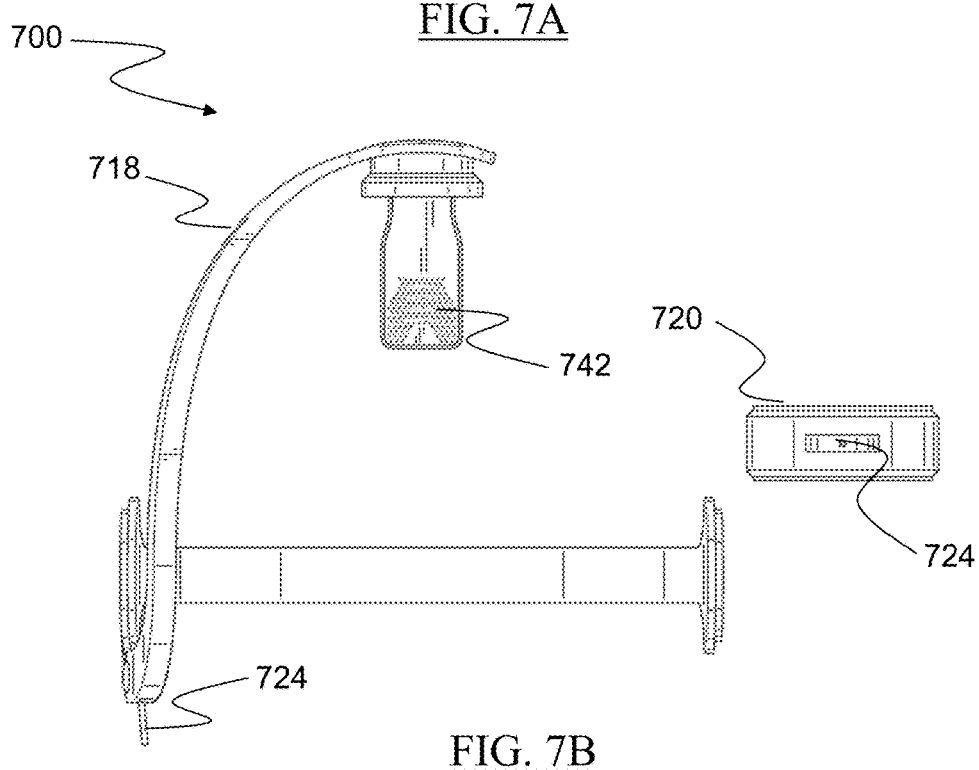

FIGS. 7A and 7B show a non-invasive neurostimulation system 700. The non-invasive neurostimulation system 700 includes headband 718, a controller 720, an intensity setting wheel 722, a mouthpiece 740, an electrode array 742, and a cable 724. The controller 720 is in electrical communication with the mouthpiece 740 and the electrode array 742 via the cable 724. During operation, a patient rests the headband 718 along an upper circumference of his/her head and inserts the mouthpiece 740 into his/her mouth. The patient can increase the intensity of the electrical signals delivered to the mouthpiece 740 by rotating the intensity setting wheel in a clockwise direction. The patient can decrease the intensity of the electrical signals delivered to the mouthpiece 740 by rotating the intensity setting wheel in a counterclockwise direction. Operation of the non-invasive neurostimulation system 700 is otherwise similar to that described above in reference to FIGS. 5A and 5B where similarly referenced elements have the same functionality (e.g. controller 720 has the same functionality as controller 520 etc.). In some embodiments, the headband 718 is configured to allow the patient to wear his/her glasses during an NINM therapy session.

Figure 8A:
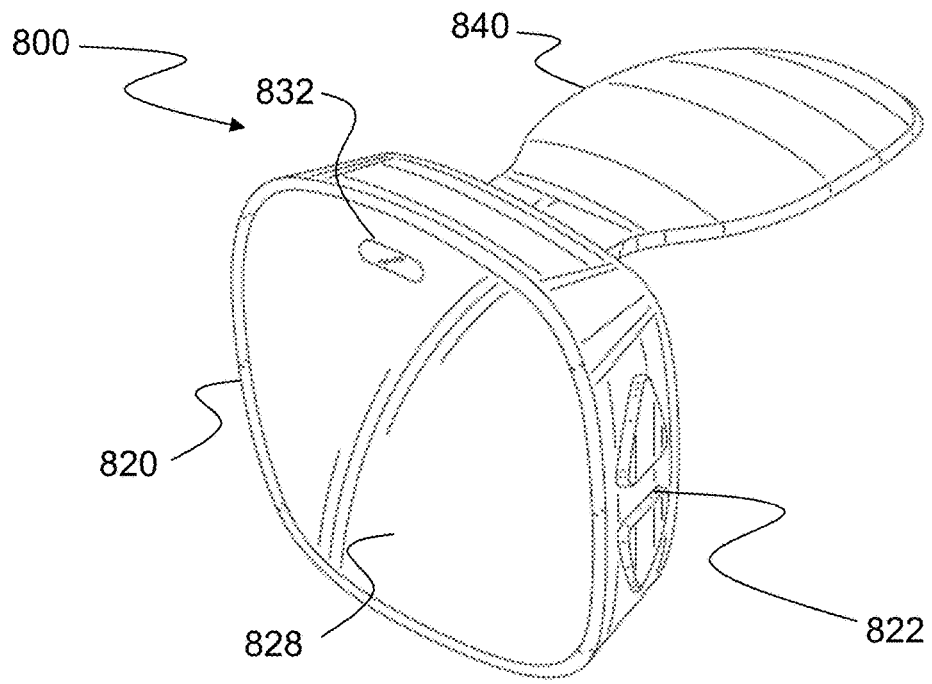
FIGS. 8A and 8B are diagrams showing a neurostimulation system according to an illustrative embodiment of the invention.
Figure 8B:
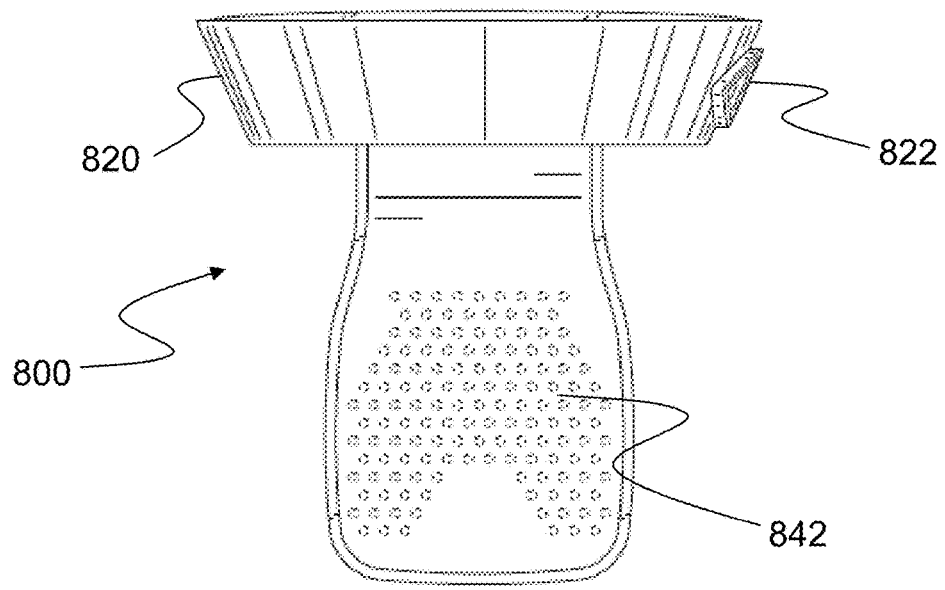

FIGS. 8A and 8B show a non-invasive neurostimulation system 800. The non-invasive neurostimulation system 800 includes a controller 820, a mouthpiece 840, pushbuttons 822, display screen 828, and indicator light 832. The controller 820 and the mouthpiece 840 are integrated into a monolithic package. The controller 820 is in electrical communication with the mouthpiece 840 and the electrode array 842. During operation, a patient inserts the mouthpiece 840 into his/her mouth and the rigidly attached controller 820 rests just outside of the patient's mouth. Operation of the non-invasive neurostimulation system 800 is otherwise similar to that described above in reference to FIGS. 5A and 5B where similarly referenced elements have the same functionality (e.g. controller 820 has the same functionality as controller 520 etc.). In some embodiments, the controller 820 is in mechanical contact with the patient's chin and is configured to mechanically secure the mouthpiece 840 during an NINM therapy session. In some embodiments, a display screen 828 is not included with non-invasive neurostimulation system 800. In some embodiments, a display screen 828 is replaced with an auditory indicator that provides auditory messages to the patient. In some embodiments, the controller 820 and the mouthpiece 840 are each monolithic and connected at a connection point between the mouthpiece 840 and the controller 820. In some embodiments, the mouthpiece 840 is removably attached to the controller 820 and can be replaced at predetermined usage intervals or upon wearing out.

FIG. 9A shows a method of operation 900 of the non-invasive neurostimulation device illustrated in FIGS. 5-8. Initially a patient connects a mouthpiece to a controller or mobile device (step 904). The connection can be a wired or wireless connection. A processor within the controller or mobile device generates a numeric sequence and transmits the generated sequence to the mouthpiece (step 908). The numeric sequence generated at step 908 can be a sequence of random values, produced by a software pseudorandom number generator, or by a hardware random number generator. Based on the received numeric sequence and a secret key shared between the mouthpiece and the controller, a processor located within the mouthpiece generates a first hash code (step 912). The first hash code can be generated using an HMAC (keyed-hash message authentication code) algorithm. In some embodiments, the first hash code is generated in accordance with an SHA-256 algorithm. The mouthpiece then transmits the first hashcode to the controller (step 916). A processor located within the controller generates a second hash code based on the shared secret key and the numeric sequence (step 920) and then compares the first hash code with the second hash code (step 924). The numeric sequence generated at step 920 can be a sequence of random values, produced by a software pseudorandom number generator, or by a hardware random number generator. In some embodiments, the second hash code is generated in accordance with an SHA-256 algorithm. If the first hash code matches the second hash code, then electrical communications are enabled between the controller and the mouthpiece (step 928). The patient then inserts the mouthpiece into his/her mouth bringing the mouthpiece into contact with the patient's intraoral cavity (step 932). Electrical neurostimulation signals can then be delivered by the controller via the mouthpiece to the patient's intraoral cavity (step 936).

FIG. 9B shows another method of operation 939 of the non-invasive neurostimulation device as shown in FIGS. 5-8 in accordance with an embodiment of the invention. Initially, a patient connects a mouthpiece to a controller or mobile device (step 940). The connection can be a wired or wireless connection. At the time of manufacture, a first hash code is generated based on a unique serial number and a secret key shared between the mouthpiece and the controller (step 944). The first hash code can be generated by an HMAC (keyed-hash message authentication code) algorithm. In some embodiments, the first hash code is generated in accordance with an SHA-256 algorithm. The first hash code and the unique serial number are stored in memory within the mouthpiece. The mouthpiece then transmits the first hash code and the unique serial number to the controller (step 948). The controller generates a second hash code based on the received unique serial number and the shared secret key (step 952). The second hash code can be generated by an HMAC (keyed-hash message authentication code) algorithm. In some embodiments, the second hash code is generated in accordance with an SHA-256 algorithm. The controller then compares the second hash code and the first hash code. The controller only permits continued electrical communications with the mouthpiece if the second hash code and the first hash code match (step 956). The patient then inserts the mouthpiece into his/her mouth bringing the mouthpiece into contact with the patient's intraoral cavity (step 960). Electrical neurostimulation signals can then be delivered by the controller via the mouthpiece to the patient's intraoral cavity (step 964).

FIGS. 10A-10D shows a controller 1020 that is configured to substantially conform to a patient's shoulders and/or neck regions as shown in FIG. 1. The controller 1020, having a length L (e.g., in some embodiments the length L can be in the range of 180-250 mm), includes an anterior portion 1060, a posterior portion 1064, and two arms 1062 that provide a separation between the anterior portion 1060 and the posterior portion 1064. The controller 1020 also includes a mouthpiece port 1016, an intensity-up button 1008, an intensity-down button 1012, a power button 1021, an info button 1024, a start/stop button 1004 and a display 1028. The posterior portion 1064 has a first radius of curvature 1034 in a transverse plane of a patient and a second radius of curvature 1036 in the transverse plane of the patient. For example, in some embodiments the first radius of curvature 1034 can be in the range of 20-50 mm and the second radius of curvature 1036 can be in the range of 15-35 mm. The two arms 1062 are separated by a distance $W_1$, and have a first radius of curvature 1030 in a sagittal plane of the patient and a second radius of curvature 1032 in a transverse plane of the patient. For example, in some embodiments the first radius 1030 can be in the range of 100-400 mm, the second radius of curvature 1032 can be in the range of 300-500 mm, and the distance $W_1$ can be in the range of 90-150 mm. Each of the arms 1062 has a central portion 1050 that is configured to contact the patient's neck and/or shoulders. The anterior portion 1060, having an opening with a width $W_2$, can have a first mass $m_1$ and be located at a first distance $d_1$ from the central portion 1050 of the arms 1062 and the posterior portion 1064 can have a second mass $m_2$ and be located at a second distance $d_2$ from the central portion 1050 of the arms 1062. In some embodiments, $m_1$ can be in the range of 15-45 g and $m_2$ can be in the range of 50-80 g. In some embodiments, $m_1$ can be approximately 25 g and $m_2$ can be approximately 60 g. The distances d1, d2, and the masses m1, m2 can be chosen such that the controller conforms or substantially conforms to the patient's shoulders and/or neck as shown in FIG. 1. In some embodiments, the product of $d_1$ and $m_1$ is larger than the product of $d_2$ and $m_2$. In some embodiments, $m_1$ and $m_2$ are approximately equal and $d_1$ is larger than $d_2$, such that $m_1 \cdot d_1 > m_2 \cdot d_2$. In some embodiments, $m_1$ is less than $m_2$ and $d_1$ is larger than $d_2$, such that $m_1 \cdot d_1 > m_2 \cdot d_2$. In some embodiments, $m_1$ is greater than $m_2$ and $d_1$ is larger than $d_2$, such that $m_1\ d_1 > m_2 \cdot d_2$. In some embodiments, $d_1$ and $d_2$ are approximately equal and $m_1$ is larger than $m_2$, such that $m_1 \cdot d_1 > m_2 \cdot d_2$. In some embodiments, $d_1$ is less than $d_2$ and $m_1$ is larger than $m_2$, such that $m_1 \cdot d_1 > m_2 \cdot d_2$. In some embodiments, the first mass is in the range of 15-35 g, the second mass is in the range of 60-65 g, the first distance is in the range of 110-140 mm, and the second distance is in the range of 30-70 mm. In some embodiments, the ratio of the second mass to the first mass is approximately 2.5 and the ratio of the first distance to the second distance is approximately 3. The controller 1020 operates similarly to controller 520 as described herein.

The terminology used herein is for the purpose of describing particular embodiments and is not intended to be limiting of the inventive concepts. It will be understood that, although the terms first, second, third etc. are used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present application.

While the present inventive concepts have been particularly shown and described above with reference to exemplary embodiments thereof, it will be understood by those of ordinary skill in the art, that various changes in form and detail can be made without departing from the spirit and scope of the present inventive concepts described and defined by the following claims.

What is claimed is:

1. A system for providing neurorehabilitation to a patient, the system comprising a mouthpiece and a controller, the mouthpiece receiving electrical neurostimulation signals from the controller and selectively delivering the received electrical neurostimulation signals to the patient, the mouthpiece comprising:
    an elongated housing having an anterior region and a posterior region, the elongated housing having a non-planar exterior top surface;
    a printed circuit board mounted to a bottom portion of the elongated housing, the printed circuit board having a plurality of electrodes for delivering subcutaneous local electrical stimulation to the patient's tongue;
    control circuitry mounted within a top portion of the elongated housing for controlling electrical signals delivered to the electrodes;
    a memory mounted within a top portion of the elongated housing; and
    a processor mounted within the top portion of the elongated housing, the processor configured to:
        (i) receive a numeric sequence from the controller,
        (ii) generate a first hash code based on the received numeric sequence and a secret key stored in the memory, wherein the secret key is shared between the mouthpiece and the controller,
        (iii) transmit the first hash code to the controller, and
        (iv) receive communications from the controller only if a second hash code based on the numeric sequence and the shared secret key generated at the controller matches the first hash code; and
    wherein the controller comprises:
        an elongated u-shaped element configured to rest upon the patient's shoulders;
        an electronic receptacle located at a terminus of the u-shaped element connecting to the cable;
        a microcontroller located within the three-dimensional u-shaped element, the microcontroller configured to send electrical control signals to the mouthpiece, the electrical control signals determining an amplitude and duration of electrical signals delivered to the patient's tongue; and
        at least one of (i) an accelerometer for measuring an activity level of the patient, (ii) a data logger for logging information related to the activity level of the patient, (iii) tongue sense circuitry for determining if a patient's tongue is in contact with the plurality of electrodes located on the bottom portion of the mouthpiece, (iv) a clock for determining a total time of usage of the mouthpiece, or (v) an audio indicator that can warn the patient when the remaining battery charge is inadequate to complete a therapy session.

2. The mouthpiece of claim 1 wherein the first hash code is an SHA-256 hash code.

3. The mouthpiece of claim 1 wherein the second hash code is an SHA-256 hash code.

4. The system of claim 1 wherein the numerical sequence comprises a sequence of random values.

5. The system of claim 4 further comprising a hardware random number generator configured to generate the numerical sequence.

6. A system for providing neurorehabilitation to a patient, the system comprising a mouthpiece and a controller, the mouthpiece receiving electrical neurostimulation signals from the controller and selectively delivering the received electrical neurostimulation signals to the patient, the mouthpiece comprising:
    an elongated housing having an anterior region and a posterior region, the elongated housing having a non-planar exterior top surface;
    a printed circuit board mounted to a bottom portion of the elongated housing, the printed circuit board having a plurality of electrodes for delivering subcutaneous local electrical stimulation to the patient's tongue;

control circuitry mounted within a top portion of the elongated housing for controlling electrical signals delivered to the electrodes;
a memory mounted within the top portion of the elongated housing;
and a processor mounted within the top portion of the elongated housing, the processor configured to
  (i) store a first hash code and a unique serial number, the first hash code based on the unique serial number and a secret key shared between the mouthpiece and the controller,
  (ii) transmit the first hash code and the unique serial number to the controller, and
  (iii) receive communications from the controller only if a second hash code based on the unique serial number and the shared secret key generated at the controller matches the first hash code; and
wherein the controller comprises:
  an elongated u-shaped element configured to rest upon the patient's shoulders;
  an electronic receptacle located at a terminus of the u-shaped element connecting to the cable;
  a microcontroller located within the three-dimensional u-shaped element, the microcontroller configured to send electrical control signals to the mouthpiece, the electrical control signals determining an amplitude and duration of electrical signals delivered to the patient's tongue; and
  at least one of (i) an accelerometer for measuring an activity level of the patient, (ii) a data logger for logging information related to the activity level of the patient, (iii) tongue sense circuitry for determining if a patient's tongue is in contact with the plurality of electrodes located on the bottom portion of the mouthpiece, (iv) a clock for determining a total time of usage of the mouthpiece, or (v) an audio indicator that can warn the patient when the remaining battery charge is inadequate to complete a therapy session.

7. The mouthpiece of claim 6 wherein the first hash code is an SHA-256 hash code.

8. The mouthpiece of claim 6 wherein the second hash code is an SHA-256 hash code.

9. The system of claim 6 wherein the numerical sequence comprises a sequence of random values.

10. The system of claim 9 further comprising a hardware random number generator configured to generate the numerical sequence.

* * * * *

UNITED STATES PATENT AND TRADEMARK OFFICE
CERTIFICATE OF CORRECTION

PATENT NO. : 10,258,790 B2
APPLICATION NO. : 15/484077
DATED : April 16, 2019
INVENTOR(S) : Guarraia et al.

Page 1 of 1

It is certified that error appears in the above-identified patent and that said Letters Patent is hereby corrected as shown below:

On the Title Page

Delete Item "(73) Assignee: Helius Medical, Inc., Newtown, PA (US)" and insert --(73) Assignee: Helius Medical, Inc, Newtown, PA (US)--

Signed and Sealed this
Twenty-third Day of July, 2019

Andrei Iancu
*Director of the United States Patent and Trademark Office*